United States Patent [19]

Wong et al.

[11] Patent Number: 5,770,407
[45] Date of Patent: Jun. 23, 1998

[54] PROCESS FOR PREPARING NUCLEOTIDE INHIBITORS OF GLYCOSYLTRANSFERASES

[75] Inventors: Chi-Huey Wong, Rancho Santa Fe, Calif.; Takashi Hayashi, Fushimi-ku, Japan

[73] Assignee: The Scripps Research Institute, La Jolla, Calif.

[21] Appl. No.: 763,227

[22] Filed: Dec. 10, 1996

[51] Int. Cl.$^6$ .............................. C12Q 1/48; C12P 19/30; C07H 1/00
[52] U.S. Cl. ............................. 435/89; 435/15; 536/55.3
[58] Field of Search ....................... 435/89, 15; 536/55.3

[56] References Cited

PUBLICATIONS

Withers, et al., "2–Deoxy–2–fluoro–D–glycosyl Fluorides", J. Biol. Chem., 263:7929–7932 (1988).
McCarter, et al., "5–Fluor Glycosides: A New Class of Mechanism–Based . . . ", J. Am. Chem. Soc., 118:241–242 (1996).
Qiao, et al., "Synergistic Inhibition of Human . . . ", J. Am. Chem. Soc., 118:7653–7662 (1996).
Murray, et al., "Mechanism and Specificity of Human . . . ", Biochemistry, 35:11183–11195 (1996).
Sinnott, Michael, "Catalytic Mechanisms of Enzymic Glycosyl Transfer", Chem. Rev., 90:1171–1202 (1990).
White, et al., "Crystallographic Observation of a Covalent Catalytic . . . ", Nature Structural Biology, 3:149–154 (1996).
Withers, et al., "Identification of a Covalent alpha–D–. . . ", J. Am. Chem. Soc., 110:8551–8553 (1988).
Withers, et al., "Unequivocal Demonstrations of the Involvement of a . . . ", J. Am. Chem. Soc., 112:5887–5889 (1990).
Ichikawa, et al., "Chemical–Enzymatic Synthesis and Conformational . . . ", J. Am. Chem. Soc., 114:9283–9298 (1992).
Adelhorst, et al., "Large–Scale Synthesis of Beta–L–fucopyranosyl . . . ", Carbohydrate Research, 242:69–76 (1993).
Gokhase, et al., "Chemical Synthesis of GDP–Fucose . . . ", Can. J. Chem., 68:1063–1071 (1990).
Veeneman, et al., "An Approach towards the synthesis of 1,2–trans . . . ", Tetrahedron Letters, 43:6175–6178 (1991).
Moffatt, J.G., "Sugar Nucleotide Synthesis . . . ", Meth. Enzymol., 8:136–142 (1966).
Roseman, et al., "Nucleoside Polyphosphates . . . ", J. Am. Chem. Soc., 83:659–663 (1961).
Heidlas, et al., "Nucleoside Phosphate Sugars: Syntheses . . . ", Acc. Chem. Res., 25:307–314 (1992).
Kochetkov, et al., "Glycosyl Esters of Nucleoside Pyrophosphates", Adv. Carbo. Chem. Biochem., 28:307–399 (1973).
Hoard, et al., "Conversion of Mono– andOligodeoxyribonucleotides . . . ", J. Am. Chem. Soc., 87:1785–1788 (1965).
Simon, et al., "Convenient Syntheses . . . ", J. Org. Chem., 55:1834–1841 (1990).
Moffatt, et al., "The Total Synthesis of Coenzyme A", J. Am. Chem. Soc., 81:1265 (1959).
Moffatt, et al., "Nucleoside Pholyphosphates . . . ", J. Am. Chem. Soc., 83:649–658 (1961).
Wong, et al., "Enzyme–Catalyzed Synthesis of N–Acetyllactosamine . . . ", J. Org. Chem., 47:5416–5418 (1982).
Stiller, et al., "Enzymatic Synthesis of Beta–L–Fucose–1–phosphate . . . ", Liebigs Ann. Chem., 467–471 (1992).

Primary Examiner—Gary L. Kunz
Attorney, Agent, or Firm—Donald G. Lewis

[57] ABSTRACT

Nucleotide linked 2-deoxy-2-fluoroglycosides are employed as potent competitive inhibitors of glycosyltransferases. More particularly, uridine-5'-diphospho-2-deoxy-2-fluorogalactose (UDP-2F-Gal), guanidine-5'-diphospho-2-deoxy-2-fluoro-L-fucose (GDP-2F-Fuc), uridine-51-diphospho-2-deoxy-2-fluoro-D-glucose (UDP-2F-Glu), guanosine-5'-diphospho-2-deoxy-2-fluoro-D-mannose (GDP-2F-Man), cytosine-5'-monophospho-2-deoxy-2-fluoro-D-sialic acid, and cytosine-5'-monophospho-2-deoxy-2-KDO may be employed as inhibitors of β-1,4-galactosyltransferase, α-1, 3-fucosyltransferase, glucosyltransferases, N-acetylglucosaminyltransferases, (α-mannosyltransferases, α-sialyltransferases, and KDO-transferases, respectively. Synthesis of nucleotide-linked-2-deoxy-2-fluoroglycosides is achieved using either chemoenzymatic or chemical methodologies.

27 Claims, 15 Drawing Sheets

PROCESS FOR PREPARING NUCLEOTIDE INHIBITORS OF GLYCOSYLTRANSFERASES

GOVERNMENT RIGHTS

This invention was made with government support under Grant No. GM 44154 awarded by the National Institutes of Health and Grant No. Che 931-0081 from the National Science Foundation. The U.S. government has certain rights in the invention.

SPECIFICATION

1. Field of the Invention

The invention relates to glycosyltransferase inhibitors. More particularly, the invention relates to nucleotide-linked-2-deoxy-2-fluoroglycosides as inhibitors of glycosyltransferases and to chemo-enzymatic and chemical methods for synthesizing such compounds.

2. Background

Sugar nucleotide-dependent glycosyltransferases which catalyze the transfer of a sugar from nucleotide to specific oligosaccharides are a group of enzymes with great potential as catalysts for complicated oligosaccharide synthesis and as targets for inhibition (Beyer et al. *Adv. Enzyniol.* 1981, 52, 23). Although several glycosyltransferases have been studied with regard to their specificities and synthetic applications, these is only limited number of studies on the inhibition and mechanism of these enzymes (Ichikawa et al. *J. Am. Chem. Soc.* 1992, 114, 9283; Vaghefi et al. *J. Med. Chem.* 1987, 30, 1383; Vaghef et al. *J. Med. Chem.* 1987, 30, 1391; Marchase et al. *Anal. Biochem.* 1991, 197, 40; Hindsgaul et al. *J. Biol. Chem.* 1991, 266, 17858; Yuasa et al. *J. Am. Chem Soc.* 1992, 114,5891; Kajihara et al. *Carbohydr. Res.* 1992, 229, C5), and in most cases the inhibitors reported are relatively weak with $K_i$ in the mM range.

Replacement of the 2-hydroxyl group of glycosyl analogs by a strongly electron-withdrawing atom such as fluorine has a large decelerating effect on glycosidase catalyzed hydrolysis, and thus 2-fluoroglycosides have been used as mechanism-based glycosidase inhibitors which form a covalent adduct (Withers et al. *J. Biol. Chem.* 1988, 263, 7929; McCarter et al. *J. Am. Chem. Soc.* 1996, 118, 241).

The β-1,3-fucosylated oligosaccharide structures are central to numerous cell-cell interactions (Ichikawa et al. (1994) *Chemistry in Britain*, 117–121.) such as inflammation, tumor development and blood clotting (Foxall et al. (1992) *J. Cell. Biol.* 117, 895–902.). Five distinct human α-1,3-fucosyltransferases have been cloned (Kukowska-Latallo et al.(1990) *Genes Dev.* 4, 1288) and shown to have different acceptor sugar specificity. α-1,3-Fucosyltransferase V (FucT V) is responsible for the terminal step in the biosynthesis of Lewis x ($Le^x$) and sialyl Lewis x ($sLe^x$), a tetrasaccharide ligand involved in inflammatory cell adhesion and metastasis (Lasky, L. A. (1992) *Science* 258, 964–969). Thus inhibition of this enzyme may impede inflammation or cancer progression, and understanding the mechanism of FucT V may lead to the development of effective inhibitors.

The α-1,3-fucosyltransferase V catalyzed reaction proceeds with inversion of configuration at the anomeric center of L-fucose (Weston et al., 1992a). Product inhibition studies have been used to establish that FucT V has an ordered, sequential, BiBi mechanism with guanosine 5'-diphospho-b-L-fucose (GDP-Fuc) binding first and the product GDP releasing last (Qiao et al.(1996) *J. Am. Chem. Soc.* 118, 7653–7662). FucT V has been shown to have a catalytic residue with $pKa_a$=4.1, presumably an active site carboxylate residue (Murray et al. (1996) *Biochemistry* 35, 11183–11195). A solvent isotope effect was observed ($D_v$=2.9, $D_{V/K}$=2.1) and exploited in a proton inventory study to show that there is a one-proton transfer in the transition state (Murray et al. (1996) *Biochemistry* 35, 11183–11195). The transition-state structure of glycosyltransferase-catalyzed reactions has been proposed to have a flattened half-chair conformation with substantial oxocarbenium ion character at the anomeric position (Kim et al., 1988, Murray et al., 1996), analogous to that of the glycosidase reactions (Sinnott, M. L. (1990) *Chem. Rev.* 90, 1171–1202). Consistent with this proposition is that fluoroglycosides have been used to probe the mechanism of glycosidases (McCarter et al. (1996) *J. Am. Chem. Soc.* 118, 241–242; White et al.(1996) *Nature Structual Biology* 3, 149–154; Withers et al. (1988) *J. Biol. Chem.* 263, 7929; Withers et al. (1988) *J. Am. Chem. Soc.* 110, 8551; Withers et al. (1990) *J. Am. Chem. Soc.* 112, 5887). Replacement of the 2- or 5-hydroxyl group of glycosyl analogs with the strong electron withdrawing group fluorine transforms the parent glycoside into a slow substrate for retaining glycosidases. These compounds have been used as mechanism based glycosidase inactivators which form a covalent adduct in the enzyme active site. The proposed transition-state structure of FucT V is also supported by the observation that aza sugars which mimic the charge distribution of the glycosyl cation are inhibitors of FucT V, and synergistic inhibition by the combination of an aza sugar, GDP, and the acceptor sugar to mimic the transition-state structure has been illustrated (Ichikawa et al. (1992a) *J. Am. Chem. Soc.* 114, 9283–9298).

With the discovery of many fucosyltransferases, the limiting step in the study of these important enzymes is the synthesis of GDP-Fuc and analogs. Unlike other sugar nucleotides, the enzymatic preparation of GDP-Fuc has not been established on large scale, and as such, several groups have reported the chemical synthesis of this substrate (Adelhorst et al.(1993) *Carbohydr. Res.* 242, 69–76; Gokhale et al. (1990) *Can. J. Chem.* 68, 1063–1071; Nunez et al.(1981) *Can. J. Chem.* 59, 2086–2095; Veeneman et al.(1991) *Tetrahedron Lett.* 32, 6175–6178). A key step in most of these procedures is the coupling of β-L-fucopyranosyl phosphate with the commercially available guanosine 5'-monophospho-morpholidate (GMP-morpholidate) (Moffatt et al.(1966) *Methods Enzymol.* 8, 136–142; Moffatt et al.(1961) *J. Am. Chem. Soc.* 83, 659–663). While the fucosyl phosphate is obtainable in a high overall yield from L-fucose (82%, five steps) using the published procedures(Adelhorst & Whitesides, 1993, Ichikawa et al., 1992b), the morpholidate coupling is a slow and low-yielding reaction and therefore not satisfactory. What is needed are nucleotide-linked-2-deoxy-2-fluoroglycosides for inhibition of glycosyl transferases. Further needed are efficient methodologies for the preparation of the nucleotide-linked-2-deoxy-2-fluoroglycosides.

Most of the chemical syntheses of sugar diphosphate nucleosides (Heidlas et al. *Acc. Chem. Res.* 1992, 25, 307–314; Kochetkov et al. *Adv. Carbohydr. Chem. Biochem.* 1973, 28, 307–399) involve the coupling of a glycosyl phosphate 26 (FIG. 11) with an activated nucleoside monophosphate (NMP) (Cramer et al. *Chem. Ber.* 1962, 95, 1664; Hoard et al. *J. Am. Chem. Soc.* 1965, 87, 1785; Simon et al. *J. Org. Chem.* 1990, 55, 1834–1841; Moffatt et al. *Methods Enzymol.* 1966, 8, 136–142; Roseman et al. *J. Am. Chem. Soc.* 1961, 83, 659–663; Clark et al. *Angew. Chem. Tnt. Ed. Engl.* 1984, 76, 704; Scheit et al. *Nucleotides Analogs, Synthesis and Biological Function*; Wiley: New York, 1980).

Of the commonly used activated NMP derivatives, phosphoramidates such as phosphorimidazolidates and especially phosphoromorpholidates 27 are the most popular, the latter being introduced in 1959 by Moffatt and Khorana (Moffatt et al. *J. Am. Chem. Soc.* 1959, 81, 1265; Moffatt et al. *J. Am. Chem. Soc.* 1961, 83, 649–658). Nevertheless, the reaction between a sugar-1-phosphate and an NMP-morpholidate is very slow (reaction times of five days are usual) and yields rarely exeed 70%. GDP-Fuc, in particular, is obtained in only 20–50% yield (Nunez et al. *Can. J. Chem.* 1981, 59, 2086–2095; Gokhale et. al. *Can. J. Chem.* 1990, 68, 1063–1071; Schmidt et al. *Liebigs Ann. Chem.* 1991, 121–124; Veeneman et al. *Tetrahedron Lett.* 1991, 32, 6175–6178; Ichikawa et al. *J. Org. Chem.* 1992, 57, 2943–2946; Adelhorst et al. *Carbohydr. Res.* 1993, 242, 69–76).

In the enzymatic preparation of sugar diphosphate nucleosides, a glycosyl phosphate is reacted with a nucleoside triphosphate (NTP), catalyzed by a nucleoside diphosphate sugar pyrophosphorylase (FIG. 1) (Wong et al. *J. Org. Chem.* 1982, 47, 5416–5418; Kawaguchi; *Methods Carbohydr. Chem.* 1980, 8, 261–269; Tochikura, T.; Kawaguchi, K.; Kawai, H.; Mugibayashi, Y.; Ogata, K. *J. Fermentl. Technol.* 1968, 46, 970; Tochikura et al. *J. Fermentl. Technol.* 1968, 46, 957; Korf et al. *Synlett* 1991, 313–314; Ginsburg et al. *Adv. Enzymol.* 1964, 26, 35). The NTP may also be generated in situ in coupled enzyme reactions. In the case of GDP-Fuc, the enzymatic preparation has been carried out only on an analytical scale (Ichikawa et al. *J. Am. Chem. Soc.* 1992, 114, 9283–9298; Stiller et al. *J. Liebigs Ann. Chem.* 1992, 467–471).

What is needed is the use of a chemical agent or procedure in phosphoromorpholidate coupling reactions to give shorter reaction times (one to two days) and higher yields (76–91%).

BRIEF SUMMARY OF THE INVENTION

The invention relates to the novel nucleotide-linked-2-deoxy-2-fluoroglycosides and the synthesis of nucleotide-linked-2-deoxy-2-fluoroglycosides by chemo-enzymatic and chemical methods. Three distinct methodologies are described. As a representative example for the synthesis of nucleotide-linked-2-deoxy-2-fluoroglycosides using a chemo-enzymatic methodology, uridine 5'-diphospho-(2-deoxy-2-fluoro)galactose (UDP-2FGal) was prepared and was found to be a competitive inhibitor of β-1,4-galactosyltransferase with a $K_i$ value of 41 $\mu$M. The precursor 2-deoxy-2-fluorogalactose (2FGal) was directly synthesized from non-protected galactal in water in the presence of $XeF_2$. Galactokinase catalyzed the phosphorylation of 2FGal with ATP to 2-deoxy-2-fluorogalactose-α-1-phosphate (2FGal-1P), which in reaction with UDP-glucose catalyzed by galactose-1-phosphate uridyltransferase was converted to UDP-2FGal. Both ATP and UDP-glucose were regenerated in order to scale up the reaction and to simplify product isolation.

A second procedure is used for the synthesis of the novel nucleotide-linked-2-deoxy-2-fluoroglycosides guanosine-5'-diphospho-2-deoxy-2-fluoro-L-fucose, uridine-5'-diphospho-2-deoxy-2-fluoro-D-glucose and guanosine-5'-diphospho-2-dioxy-2-fluoro-D-manose. These compounds are prepared using nonenzymatic, chemical methodologies and are potential inhibitors of α-fucosyltransferases, glucosyltransferases, N-acetylglucosaminyltransferases and α-mannosyltransferases respectively. The chemical procedure uses the same halohydrin procedure as that of the chemoenzymatic procedure, using water in the presence of $XeF_2$. This chemical procedure, however, uses a nonenzymatic process to couple the nucleotide to the glycoside and employs a morpholidate nucleotide substrate with 1-H-tetrazole for coupling the nucleotide to a chemically derived glycosyl dibenzyl phosphate, in lieu of the use of a transferase onto an enzymatically derived glycosyl phosphate as found in the first procedure. One of the chemically prepared compounds, GDP-2-deoxy-2-fluoro-L-fucose (GDP-2F-Fuc, 21) was tested for inhibition and found to be a potent competitive inhibitor of α 1,3-fucosyltransferase V with $K_i$ values of 4.2 $\mu$M.

A third chemoenzymatic procedure is included for the preparation of the nucleotide-linked-2-deoxy-2-fluoroglycosides cytosine-5'-monophospho-2-deoxy-2-fluoro-D-sialic acid and cytosine-5'-monophospho-2-deoxy-2-KDO which are inhibitors of α-sialyltransferases, and 2-keto-3-deoxyoctnate (KDO)-transferases. This third, chemoenzymatic procedure uses the same halohydrin procedure as that of the first chemoenzymatic procedure, using water in the presence of $XeF_2$. The procedure differs from the other procedures in that it does not require a phosphorylation of the glycoside. The coupling of the nucleotide to the glycoside is directly accomplished using a synthetase enzyme.

One aspect of the invention is directed to nucleotide-linked 2-deoxy-2-luoroglycosides. Preferred nucleotide-linked 2-deoxy-2-luoroglycosides include uridine 5'-diphospho-(2-deoxy-2-fluoro)-D-galactose; guanosine-5'-diphospho-2-deoxy-2-fluoro-L-fucose; uridine-5'-diphospho-2-deoxy-2-fluoro-D-glucose; guanosine-5'-diphospho-2-deoxy-2-fluoro-D-mannose; cytosine-5'-monophospho-2-deoxy-2-fluoro-sialic acid; and cytosine-5'-monophospho-2-deoxy-2-KDO.

Another aspect of the invention is directed to chemical intermediates employed for the synthesis of nucleotide-linked 2-deoxy-2-luoroglycosides. Preferred chemical intermediates include 2-deoxy-2-fluoro-α-D-galactopyranosyl phosphate ion; 2-deoxy-2-fluoro-α-L-fucosylpyranosyl phosphate ion; 2-deoxy-2-fluoro-D-glucosylpyranosyl phosphate ion; 2-deoxy-2-fluoro-D-mannosylpyranosyl phosphate ion; 2-deoxy-2-fluoro-sialic acidpyranosyl phosphate ion; 2-deoxy-2-fluoro-KDO-pyranosyl phosphate ion; 2-deoxy-2-fluoro-D-galactose; 2-deoxy-2-fluoro-L-fucose; 2-deoxy-2-fluoro-D-glucose; 2-deoxy-2-fluoro-D-mannose; 2-deoxy-2-fluorosialic acid; and 2-deoxy-2-fluoro-KDO.

Another aspect of the invention is directed to a process for preparing a 2-deoxy-2-fluoro-glycosyl-pyranosyl phosphate. The process includes a first step for fluorohydrinating a glycal with a fluoridating agent and a hydroxylating agent for producing a 2-deoxy-2-fluoro-glycoside. The first step is then followed by a second step for phosphorylating the 2-deoxy-2-fluoro-glycoside with a phosphorylating agent for producing a 2-deoxy-2-fluoro-glycosyl-pyranosyl phosphate.

Another aspect of the invention is directed to a process for preparing a nucleotide-linked-2-deoxy-2-fluoroglycoside. The process includes a first step for phosphorylating a 2-deoxy-2-fluoro-glycoside with a phosphorylating agent for producing a 2-deoxy-2-fluoro-glycosol-pyranosol phosphate. The first step is then followed by a second step for coupling the 2-deoxy-2-fluoro-glycosyl-pyranosyl phosphate to a nucleotide with a coupling agent for producing the nucleotide-linked-2-deoxy-2-fluoroglycoside.

Another aspect of the invention is directed to a process for preparing a nucleotide-linked-2-deoxy-2-fluoroglycoside.

The process includes a first step for fluorohydrinating a glycal with a fluoridating agent and a hydroxylating agent for producing a 2-deoxy-2-fluoro-glycoside. The first step is then follow by a second step for phosphorylating the 2-deoxy-2-fluoro-glycoside with a phosphorylating agent for producing a 2-deoxy-2-fluoro-glycosyl-pyranosyl phosphate. The second step is then followed by a third step for coupling the 2-deoxy-2-fluoro-glycosyl-pyranosyl phosphate to a nucleotide with a coupling agent for producing the nucleotide-linked-2-deoxy-2-fluoroglycoside. In a preferred mode of this process, the nucleotide-linked-2-deoxy-2-fluoroglycoside is selected from the group consisting of uridine 5'-diphospho-2-deoxy-2-fluoro-D-galactose, guanosine-5'-diphospho-2-deoxy-2-fluoro-L-fucose, uridine-5'-diphospho-2-deoxy-2-fluoro-D-glucose, guanosine-5'-diphospho-2-deoxy-2-fluoro-D-mannose, cytosine-5'-monophospho-2-deoxy-2-fluoro-sialic acid and cytosine-5'-monophospho-2-deoxy-2-KDO. In another preferred mode, the glycal is selected from the group consisting of D-galactal, L-fucal, tri-o-acetyl-D-glucal, sialic acid glycal, KDO glycal. A preferred fluoridating agent is $XeF_2$. A preferred hydroxylating agent is water. Preferred 2-deoxy-2-fluoro-glycoside are selected from the group consisting of 2-deoxy-2-fluoro-D-galactose, 2-deoxy-2-fluoro-L-fucose, 2-deoxy-2-fluoro-D-glucose, 2-deoxy-2-fluoro-D-mannose, 2-deoxy-2-fluorosialic acid, 2-deoxy-2-fluoro-KDO. Preferred phosphorylating agent are selected from the group consisting of ATP with glycosylkinase and dibenzyl phosphate. Preferred 2-deoxy-2-fluoro-glycosyl-pyranosyl phosphate are selected from the group consisting of 2-deoxy-2-fluoro-α-D-galactopyranosyl phosphate, 2-deoxy-2-fluoro-α-L-fucosylpyranosyl phosphate, 2-deoxy-2-fluoro-D-glucosylpyranosyl phosphate, 2-deoxy-2-fluoro-D-mannosylpyranosyl phosphate, 2-deoxy-2-fluoro-sialic acid-pyranosyl phosphate, 2-deoxy-2-fluoro-KDO-pyranosyl phosphate. Preferred nucleotide are selected from the group consisting of uridine 5'-diphosphate, guanosine 5'-diphosphate, adenosine 5'diphosphate and cytidine 5'-diphosphate. Preferred coupling agent are selected from the group consisting of galactose-1phosphate uridyl transferase, guanosyl-mono-phosphate (GMP)-morpholidate, cytidyl -mono-phosphate (CMP)-morpholidate and uridyl-mono-phosphate (UMP)-morpholidate.

In a preferred mode, 2-deoxy-2-fluoro-glycoside is prepared according to the above process. In this instance, it is preferred to admix the glycal with $XeF_2$ followed by hydrolysis with hydrochloric acid for producing the 2-deoxy-2-fluoro-glycoside. It is further preferred to activate the 2-deoxy-2-fluoro-glycoside with acetic anhydride and then hydrobromic acid followed by phosphorylation with dibenzyl phosphate and reduction using hydrogen with Pd/C for producing the 2-deoxy-2-fluoro-glycosyl-pyranosyl phosphate. Furthermore, the 2-deoxy-2-fluoro-glycosyl-pyranosyl phosphate may be converted into a phosphate ion followed by coupling a nucleotide linked morpholidate to the phosphate ion in the presence of 1H-tetrazole wherein the nucleotide linked morpholidate is selected from the group consisting of guanosyl-mono-phosphate (GMP)-morpholidate, cytidyl-mono-phosphate (CMP)-morpholidate and uridyl-mono-phosphate (UMP)-morpholidate for producing the nucleotide-linked-2-deoxy-2-fluoroglycoside.

Another aspect of the invention is directed to a process for preparing uridine 5'-diphospho-2-deoxy-2-fluoro galactose. The process includes a first step for fluorohydrinating D-galactal with $XeF_2$ and water for producing 2-deoxy-2-fluoro-galactose. The first step is then followed by a second step for phosphorylating 2-deoxy-2-fluoro-galactose with ATP and galactokinase for producing 2-deoxy-2-fluoro-α-D-galactopyranosyl phosphate. The second step is followed by third step for coupling 2-deoxy-2-fluoro-α-D-galactopyranosyl phosphate with uridine 5'-diphosphate using galactose-1-phosphate uridyl transferase for producing uridine 5'-diphospho-2-deoxy-2-fluoro galactose. In this instance, it is preferred to admix the D-galactal with $XeF_2$ and water at room temperature followed by neutralization with potassium carbonate for producing 2-deoxy-2-fluoro-D-galactose. It is then preferred to then admix the 2-deoxy-2-fluoro-D-galactose (2FGal) with ATP, phospho(enol) pyruvate, galactokinase and pyruvate kinase in a pH 7.4 buffer solution at room temperature for producing 2-deoxy-2-fluoro-α-D-galactopyranosyl phosphate (2FGal-1P). It is then preferred to admix the 2-deoxy-2-fluoro-α-D-galactopyranosyl phosphate (2FGal-1P) with UTP, UDP glucose, galactose-1-phosphate uridyl transferase, uridine 5'-diphosphoglucose pyrophosphorylase and inorganic pyrophosphatase in a pH 8.4 buffer solution at room temperature for 3 days for producing uridine 5'-diphospho-(2-deoxy-2-fluoro)galactose (UDP-2F-Gal).

Another aspect of the invention is directed to a process for preparing a nucleotide-linked-2-deoxy-2-fluoroglycoside. The process includes a first step for fluorohydrinating a glycal with a fluoridating agent and a hydroxylating agent for producing a 2-deoxy-2-fluoro-glycoside. This first step is then followed by a second step for coupling the 2-deoxy-2-fluoro-glycosyl-pyranosyl phosphate to a nucleotide with a coupling agent for producing the nucleotide-linked-2-deoxy-2-fluoroglycoside. In this process, the preferred nucleotide-linked-2-deoxy-2-fluoroglycoside is selected from the group consisting of cytosine-5'-monophospho-2-deoxy-2-fluoro-D-sialic acid and cytosine-5'-monophospho-2-deoxy-2-KDO. The preferred glycal is selected from the group consisting of sialic acid glycal and KDO glycal. The preferred fluoridating agent is $XeF_2$ and the preferred hydroxylating agent is water. Allternatively, the 2-deoxy-2-fluoro-glycoside may be selected from the group consisting of 2-deoxy-2-fluorosialic acid and 2-deoxy-2-fluoro-KDO. Alternatively, the coupling agent is selected from the group consisting of cytidyl-mono-phosphate (CMP)-sialate synthetase, cytidyl-mono-phosphate (CMP)-KDO-synthetase. A preferred nucleotide is cytidine 5'-phosphate.

Another aspect of the invention is directed to a process for inhibiting a β-1,4-glycosyltransferase using a nucleotide-linked-2deoxy-2-fluoroglycoside. In this process, the preferred nucleotide-linked-2-deoxy-2-fluoroglycoside is selected from the group consisting of uridine 5'-diphospho-2-deoxy-2-fluoro-D-galactose, guanosine-5'-diphospho-2-deoxy-2-fluoro-L-fucose, uridine-5'-diphospho-2-deoxy-2-fluoro-D-glucose, guanosine-5'-diphospho-2-deoxy-2-fluoro-D-mannose, cytosine-5'-monophospho-2-deoxy-2-fluoro-sialic acid, cytosine-5'-monophospho-2-deoxy-2-KDO. The preferred β 1,4-glycosyl transferase is selected from the group consisting of α-fucosyl transferase, glucosyltransferase, α-mannosyltransferase, α-sialyl transferase and KDO-transferase.

DETAILED DESCRIPTION OF THE INVENTION

The invention is directed to novel nucleotide-linked, 2-deoxy-2-fluoroglycosides and to the synthesis of nucleotide-linked, 2-deoxy-2-fluoroglycosides for inhibition of glycosyltransferases. The compounds and methodologies are novel and some have been tested for inhibition to the corresponding glycosyltransferase. Uridine 5'-diphospho-2-deoxy-2-fluoro-α-D-galactose (UDP-2F-Gal, 1) was found to be a potent competitive inhibitor of β 1,4-galactosyltransferase with $K_i$ values of 41 μM and GDP-2-deoxy-2-fluoro-L-fucose (GDP-2F-Fuc, 21) was found to be a potent competitive inhibitor of α-1,3-fucosyltransferase V with $K_i$ values of 4.2 μM respectively. Other novel nucleotide-linked-2-deoxy-2-fluoroglycosides were synthesized including uridine-5'-diphospho-2-deoxy-2-fluoro-D-glucose, guanosine-5'-diphospho-2-deoxy-2-fluoro-D-mannose, cytosine-5'-monophospho-2-deoxy-2-fluoro-D-sialic acid and cytosine-5'-monophospho-2-deoxy2-KDO. There are three distinct but chemically related methodologies disclosed.

Figure 1:
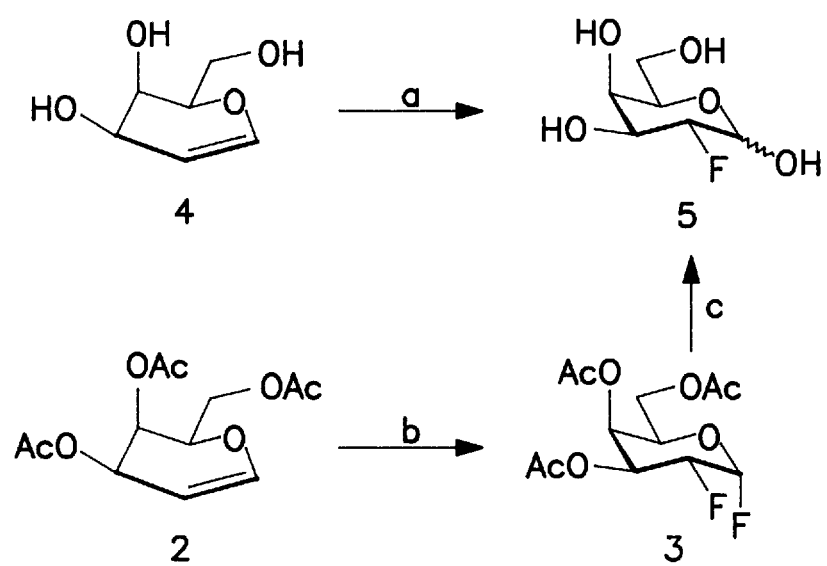
FIG. 1 illustrates the synthesis of key intermediate 2-deoxy-2-fluoro-galactose 5 from either compound 2 or compound 4 with the following steps: (a) $XeF_2$(1.8 eq), $H_2O$, room temperature, 1.5 h, 30%. a:b=1:1.5. (b) $XeF_2$, $BF_3 \cdot OEt_2$, $Et_2O$-benzene, room temperature, 2.5 h, 78%. (c) 2N HCl, 90° C., 2 h, 83%, a:b=1:1.6.
Figure 2:
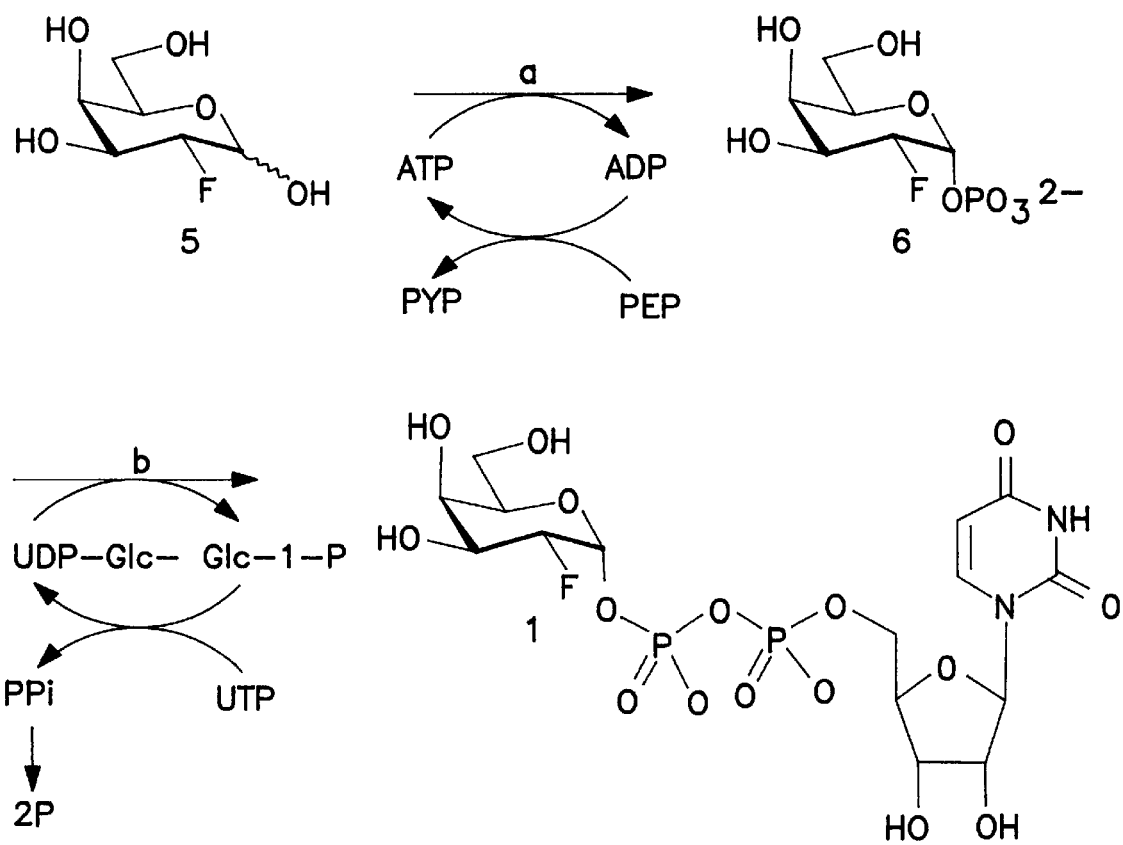
FIG. 2 illustrates the synthesis of UDP-2FGal (1) as an inhibitor of β-1,4-galacotransferase as carried out with the following steps: (a) galactokinase, pyruvate kinase, ATP.Na2, phosphoenolpyruvate.Na3 (PEP.Na3) dithiothreitol, cysteine, Mg2+, Mn2+, K+, HEPES 100 mM, pH=7.4, 4 days under Ar,room temperature, 58% yield. (b) galactose-1-phosphate uridytransferase, UDP-glucose (UDP-Glc) pyrophosphorylase, pyrophosphatase, UTP.Na3, UDP-Glc.Na2, dithiothreitol, pH=8.4, 2 days under Ar, room temperature, 67% yield.

FIGS. 1 and 2 illustrate the synthesis of 1. The key intermediate 2-deoxy-2-fluorogalactose (5) used in the enzymatic synthesis of 1 can be prepared from tri-O-acetyl-D-galactal (2) by electrophilic fluorinating reagents such as F$_2$, CF$_3$OF, AcOF etc. (Ido et al. *J. Org. Chem.* 1977, 42, 2341; Adamson et al. *Carbohydr. Res.* 1972, 22, 257; Jewett et al. *Synth. Commun.* 1984, 14, 45). These gas reagents are, however, toxic and difficult to handle. In contrast, XeF$_2$, which is available as solid, has been used in the fluorination of protected galactal 2 in the presence of a Lewis acid (Korytnyk et al. *Tetrahedron Lett.* 1980, 21, 1493; Korytnyk et al. *Tetrahedron* 1982, 38, 2547; Tius et al. *Tetrahedron* 1995, 51, 6605). The yield was improved to 78% using one equivalent of XeF$_2$ and catalytic BF$_3$.Et$_2$O in ether-benzene.

Compound 5 can be prepared directly from non-protected D-galactal in water via reaction with 1.8 equiv of XeF$_2$ at room temperature and the reaction is complete in 2 hours to give 5 as the only product in 30% yield (The initial reaction mixture was found to be acidic (pH=1.5). Prepared from 1 mmol galactal and 1.8 mmol of XeF$_2$ in 2.5 mL water. After reaction, the mixture was neutralized with K$_2$CO$_3$ and evaporated, and purified by silica gel chromatography with CHCl$_3$—MeOH (50:1 to 5:4) to give compound 5 (54.6 mg, 30%)).

Compound 5 was then enzymatically converted to 2-deoxy-2-fluoro-α-D-galactopyranosyl phosphate (2FGal-1P, 6) and to UDP-2FGal 1 as shown in FIG. 2. In the first step, galactokinase from yeast (Sigma) was found to catalyze the direct phosphorylation at the anomeric center of 5 with ATP. The reaction was coupled with phosphoenol pyruvate and pyruvate kinase in order to scale up the reaction and simplify product isolation (Ichikawa et al. *J. Am. Chem. Soc.* 1992, 114, 9283). The enzymatic reaction gave only the α-form of compound 6 in 58% yield.

Compound 1 was then prepared from 6 and UDP-glucose catalyzed by yeast galactose-1-phosphate uridyltransferase (Sigma), and the reaction was coupled with the regeneration of UDP-glucose from glucose-i-phosphate using yeast UDP-glucose pyrophosphorylase and pyrophosphatase (both are from Sigma) (Heidlas et al. *J. Org. Chem.* 1992, 57, 152; Wong et al. *J. Org. Chem.* 1992, 57, 4343). The product was further purified by ion-exchange chromatography to obtain 1 in 67% yield (71 mg).

In a representative synthesis of 1, a solution (5 mL, pH 8.4) containing 70 mg of 6, UDP-glucose (1.8 mg), UTP.Na$_3$.2H$_2$O (120 mg), Gal-1-P uridyl transferase (5U), UDP-glucose pyrophosphorylase (5U), and inorganic pyrophosphatase (5U) was incubated for 3 days. The reaction was stopped by immersing the tube into a boiling water for 90 sec and centrifuged to remove the precipitate. The supernatant was applied to a Dowex 1-X8 column (100–200 mesh, Cl$^-$ form, 1.5×25 cm), washed with water (50 mL) and the desired product was eluted from the column in a gradient of 40 mM LiCl in 3 mM HCl and 0.4M LiCl in 3 mM HCl (1.2 L). The desired fractions were adjusted to pH 6 and lyophilized, and treated with 4 mM MeOH followed by 40 mL acetone to obtained the precipitate, which was treated with MeOH and acetone again until the supernatant was free of Cl$^-$. The precipitate was then dissolved in water, treated with Dowex 50W-X-8 (H$^+$ form) and neutralized with NaOH followed by lyophilization to give 1 as sodium salt (72 mg, 67%).

Compound 1 was also prepared directly from 5 in 40% yield without isolation of 6. As shown in the NMR analysis, the axial proton at C2 position of galactose exhibits a characteristic dddd pattern at 4.633 ppm (J=49.5, 10.0, 3.5, 3.0 Hz) due to the coupling with fluorine and phosphine atoms, H1 and H3, respectively. An alternate synthesis of 1 via reaction of 6 and uridine 5'-monophosphomorpholidate was explored (Roseman et al. *J. Am. Chem. Soc.* 1961, 83, 659; Ichikawa *J. Org. Chem.* 1992, 57, 2943), however, the yield of 1 was not sufficient and it was difficult to separate 1 from UMP and unreacted 6.

Compound 1 was then evaluated as inhibitor of β 1,4-galactosyltransferase from bovine milk (Sigma) according to the procedure described previously (FIG. 3)(Ichikawa et al. *J. Am. Chem. Soc.* 1992, 114, 9283), and it was found to be a competitive inhibitor of the enzyme with $K_i$=41 μM. This result and the previous observation that the corresponding 2-deoxy derivative is a good substrate for the transferase (Wong et al. *J. Org. Chem.* 1992, 57, 4343; Srivastava et al. *Carbohydr. Res.* 1993, 245, 137) suggests that the enzymatic reaction proceeds through a oxonium-like intermediate.

Figure 9A:
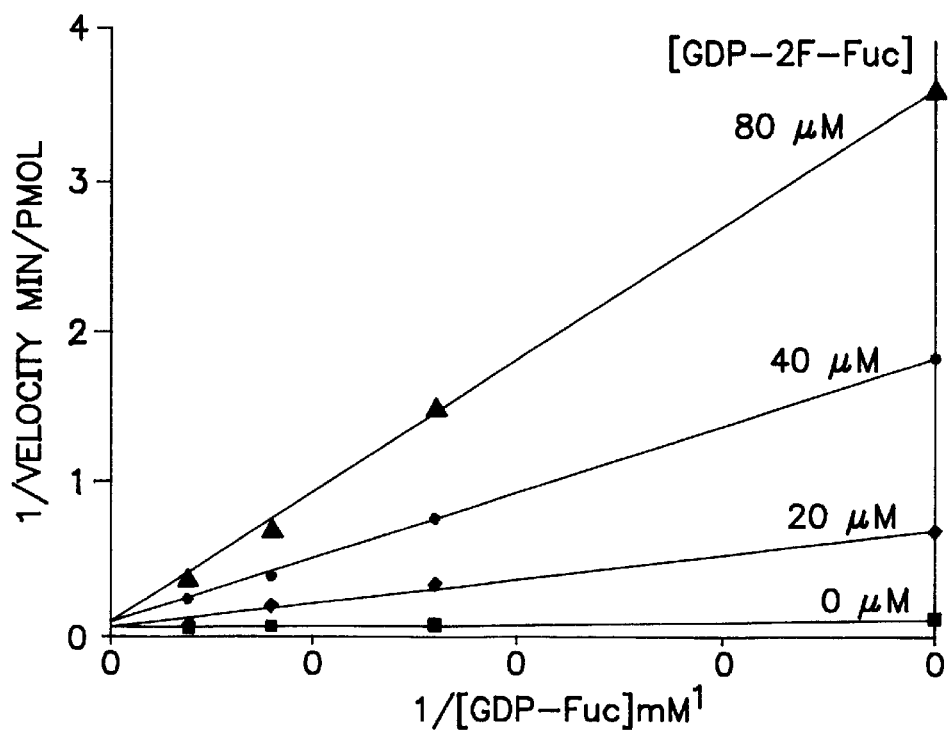
FIG. 9 illustrates a graphical $K_i$ determination in which GDP-2F-Fuc was shown to be a potent competitive inhibitor with a $K_i$=4.2±0.6 mM. GDP-Fuc concentration was varied (10, 25, 50, 100 mM) and the acceptor sugar, LacNAc-b-O—(CH$_2$)$_5$CO$_2$CH$_3$, was kept at twice its $k_m$ level, 0.6 mM. (Inset) A replot of the slopes as a function of GDP-2F-Fuc concentration is presented as a graphical $K_i$ determination ($K_i$=x axis intercept). The precise $K_i$ was determined with a nonlinear, least squares fit of the data to the equation for competitive inhibition.
Figure 9B:
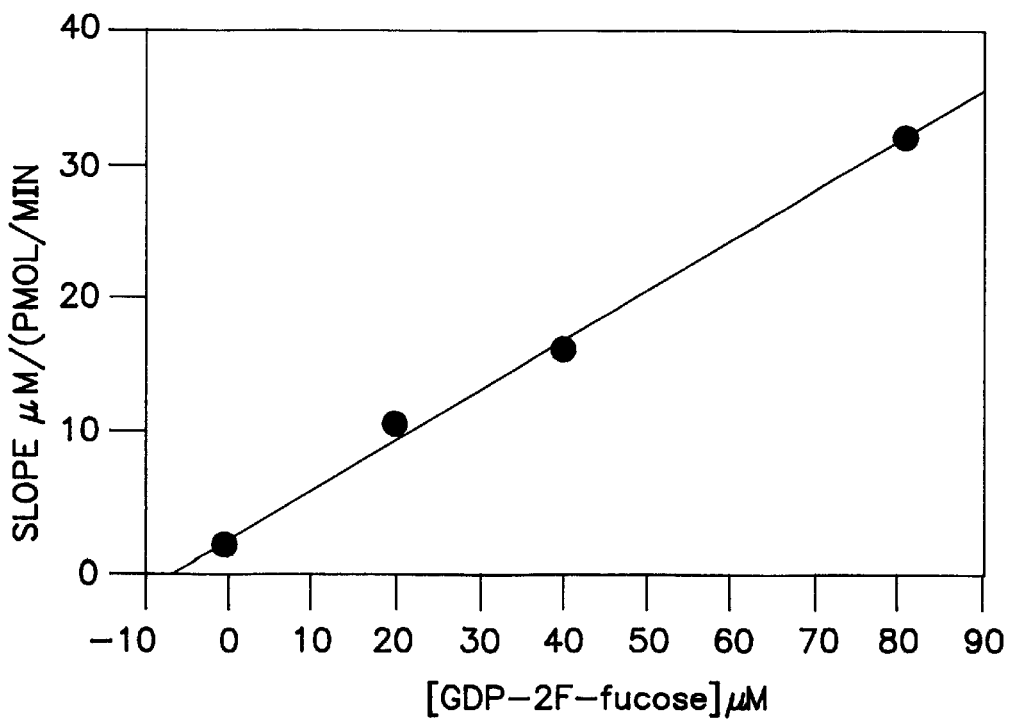
Figure 10:
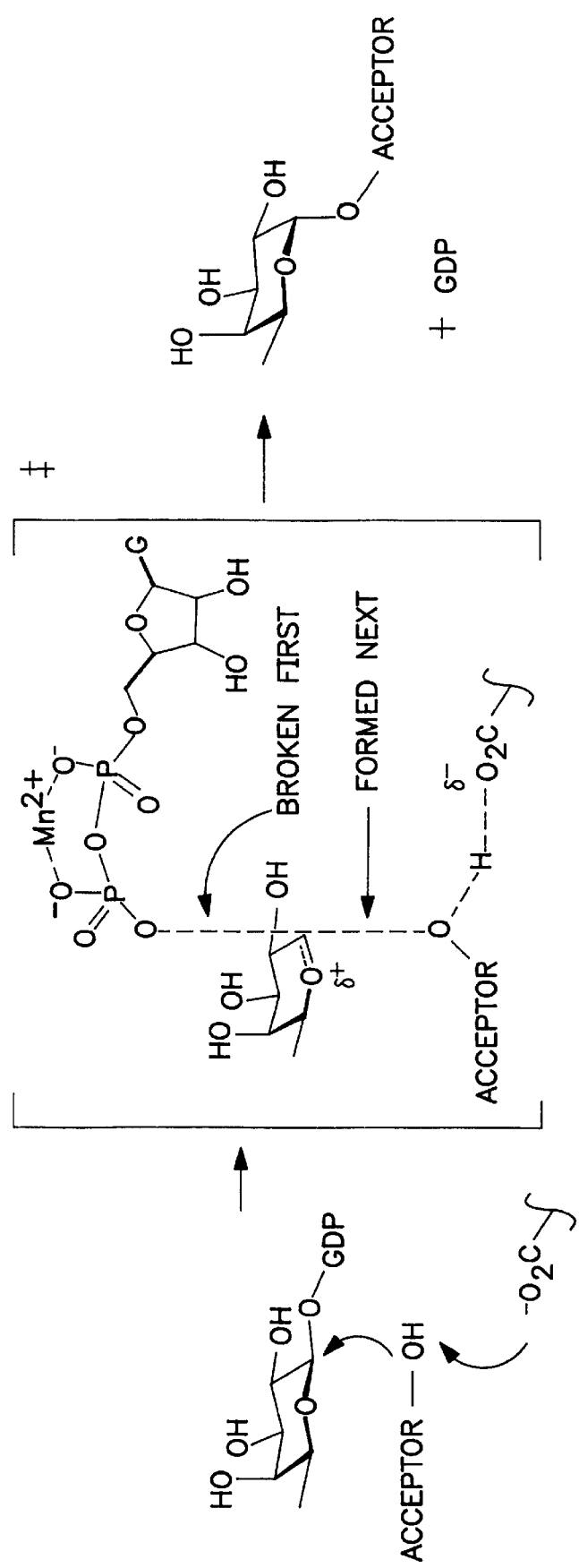
FIG. 10 illustrates a proposed mechanism for human α-1,3fucosyltransferase V reaction. Both the observation of a secondary isotope effect of GDP-[1-$^2$H]-Fuc and the inhibition of GDP-2F-Fuc are consistent with significant glycosidic bond cleavage prior to the nucleophile attack on the anomeric position of GDP-Fuc. The proton inventory study suggests one-proton transfer in the transition state.
Figure 11:
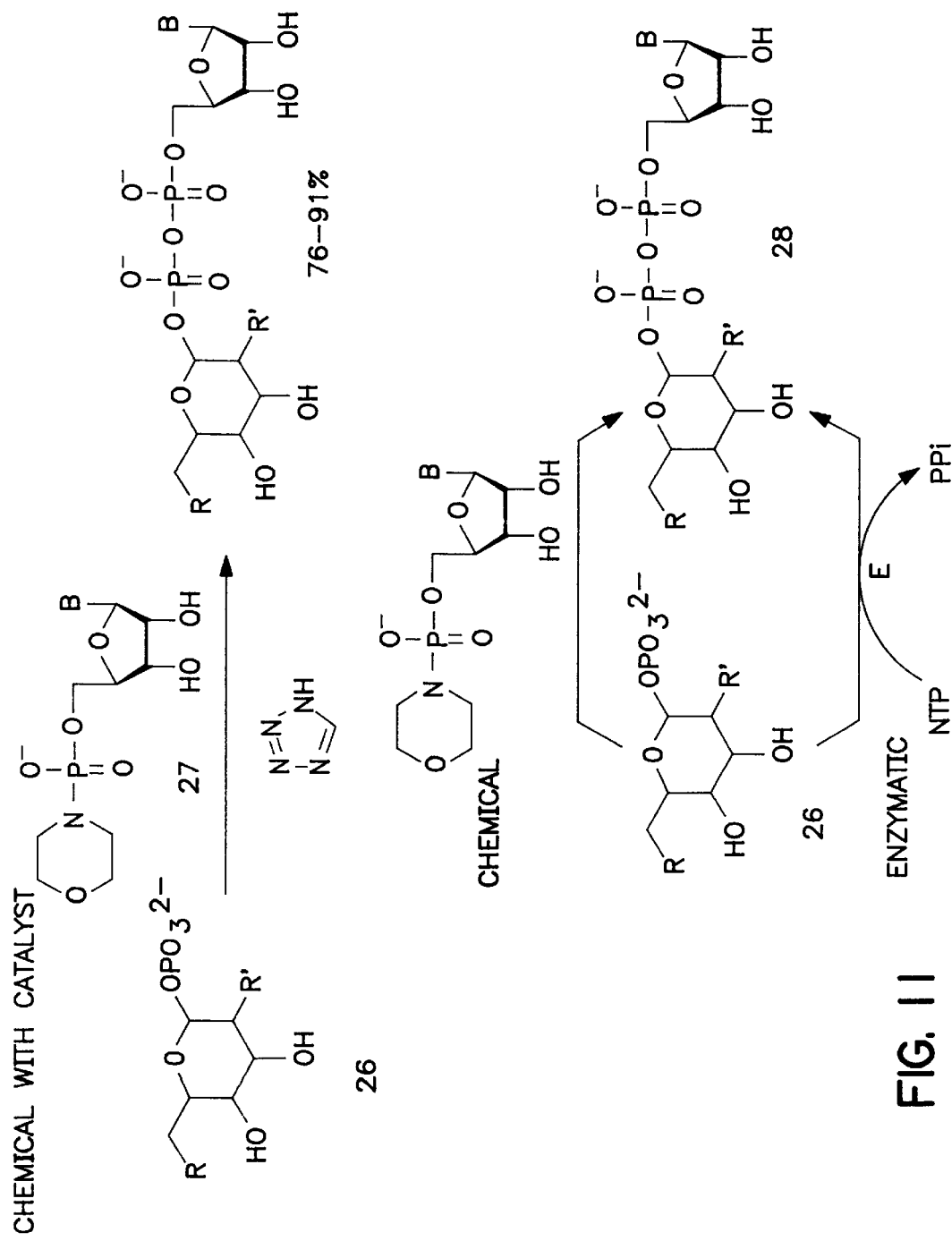
FIG. 11 illustrates both chemical and enzymatic strategies for the preparation of sugar diphosphate nucleosides. (Top) Synthesis of sugar diphosphate nucleoside using a chemical strategy wherein a glycosyl phosphate 26 is reacted with an activated nucleoside nonophosphate (NMP) 27; (Bottom) Synthesis of sugar diphosphate nucleoside using an enzymatic strategy wherein a glycosyl phosphate is reacted with a nucleoside triphosphate (NTP), catalyzed by a nucleoside diphosphate sugar pyrophosphorylase (E).

Rather than using a chemoenzymatic procedure, a non enzymatic, synthetic organic methodology was used for the synthesis of GDP-2-deoxy-2-fluoro-L-fucose (GDP-2F-Fuc, 21), uridine-5'-diphospho-2-deoxy-2-fluoro-D-glucose (UDP-2F-Glu, 16) and guanosine-5'-diphospho-2-deoxy-2-fluoro-D-mannose (GDP-2F-Man, 11). The methodology used a morpholidate based coupling using 1H-tetrazole as a catalyst. The novel sugar nucleotides GDP-2-deoxy-2-fluoro-L-fucose (GDP-2F-Fuc, 21), uridine-5'-diphospho-2-deoxy-2-fluoro-D-glucose (UDP-2F-Glu, 16) and guanosine-5'-diphospho-2-deoxy-2-fluoro-D-mannose (GDP-2F-Man, 11) (FIGS. 4–6) were obtained in high yields. GDP-2-deoxy-2-fluoro-L-fucose (GDP-2F-Fuc, 21) was used to investigate the transition-state structure of the FucT V reaction. Evidence is presented for sp$^2$ hybridization in the transition state through secondary isotope studies. In addition, the potency of inhibition of GDP-2F-Fuc is presented as evidence of the accumulation of positive charge at the anomeric position of GDP-Fuc in the transition state (FIGS. 9 and 10).

For the synthesis of 2-deoxy-2-fluoro-β-L-fucosyl phosphate 21 (Scheme 6), 3,4-Di-O-acetyl-L-fucal was converted to the acetylated 1,2-difluoro compound 17 using xenon difluoride (Korytnyk et al.(1982) *Tetrahedron* 38, 2547–2550.). Hydrolysis of 17 with hydrochloric acid and acetylation gave the 2-fluoro-L-fucose derivative 18. Treatment with hydrobromic acid followed by phosphorylation with dibenzyl phosphate and silver carbonate in benzene gave the β-L-fucosyl phosphate 19 together with a small amount of its α-anomer (α: : β=1 : 12). The benzyl groups were removed hydrogenolytically and deacetylation with cyclohexylamine in methanol gave crystalline deprotected 2-deoxy-2-fluoro-b-L-fucopyranosyl phosphate 21 as its di(cyclohexylammonium) salt. Before the coupling with GMP-morpholidate all fucosyl phosphates were converted into their triethylammonium salts by passing through a cation exchange column (Et$_3$N$^+$ form) in order to get material soluble under the conditions of the coupling reaction.

The reaction of fucosyl phosphate and GMP-morpholidate is usually carried out in pyridine but even after a reaction time of five days we were able to detect large amounts of both starting materials, as judged by TLC. As the morpholino group has to become protonated to serve as an efficient leaving group, we felt that the addition of an acid catalyst probably could enhance the outcome of the reaction. 1H-Tetrazole (pK$_a$ 4.9) is commonly used for the activation of phosphoramidites (Sim et al.(1993) *J. Am. Chem. Soc.* 115, 2260–2267) and it turned out that this heterocycle is also an efficient catalyst for the phosphoramidate coupling. Depending on the equivalents of fucosyl phosphate and GMP-morpholidate used, the reaction is complete after one or two days.

The interaction of GDP-2F-Fuc with FucT V was evaluated. The mode of inhibition of FucT V by GDP-2F-Fuc was evaluated by varying the GDP-Fuc concentrations at fixed GDP-2F-Fuc concentrations at a constant LacNAc-b-O—(CH$_2$)$_5$CO$_2$CH$_3$ concentration. The double reciprocal plot showed a competitive inhibition pattern (FIG. 9). An inhibition constant for GDP-2F-Fuc was determined to be 4.2±0.6 mM by a nonlinear least squares fit of the data to the equation for competitive inhibition. Evidence that GDP-2F-Fuc was not a slow substrate or an inactivator was obtained. Pre incubation of 0.010 mM GDP-2F-Fuc with the FucT V in the presence of LacNAc-b-O—(CH$_2$)$_5$CO$_2$CH$_3$ and MnCl$_2$ was performed for 0–80 minutes. The reactions were initiated with GDP-Fuc and allowed to react for 30 minutes. The percent inhibition remained constant at 58% which is expected for reversible inhibition. If GDP-2F-Fuc was either an inactivator of a slow substrate, then the inhibition would either increase or decrease as a function of time. This result is in contrast to the results for the hydrolysis of 2-fluoroglycosides by retaining glycosidases which form a covalent adduct in the active site, mechanism based inactivation (McCarteret al. (1993) *Carbohydr. Res.* 249, 77; Withers et al. (1988) *J. Am. Chem. Soc.* 110, 8551.).

Competitive inhibition of FucT V by guanosine 5'-diphospho-2-deoxy-2-fluoro-β-L-fucose (GDP-2F-Fuc) was observed with an inhibition constant of 4.2 mM which represents the most potent inhibitor of this enzyme to date. Incubation of GDP-2F-Fuc with FucT V and an acceptor molecule prior to the addition of GDP-Fuc had no effect on the potency of inhibition, indicating that GDP-2F-Fuc is neither an inactivator nor a slow substrate.

Figure 7:
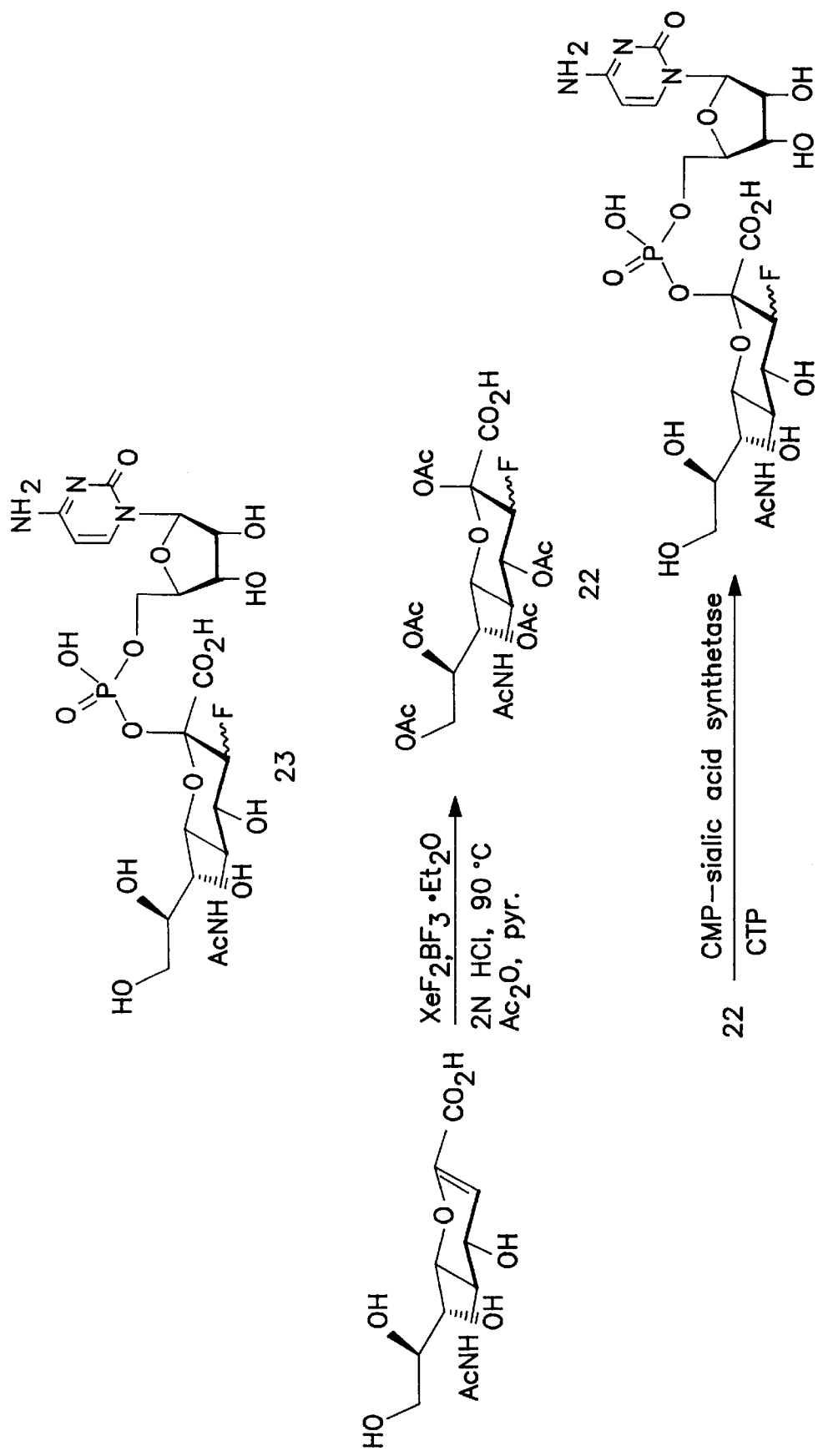
FIG. 7 illustrates the synthesis of CMP-2-fluorosialic acid (24) as an inhibitor of α-sialyltransferases as carried out with the indicated steps using CMP-sialic acid synthetase to couple nucleotide with sugar.
Figure 8:
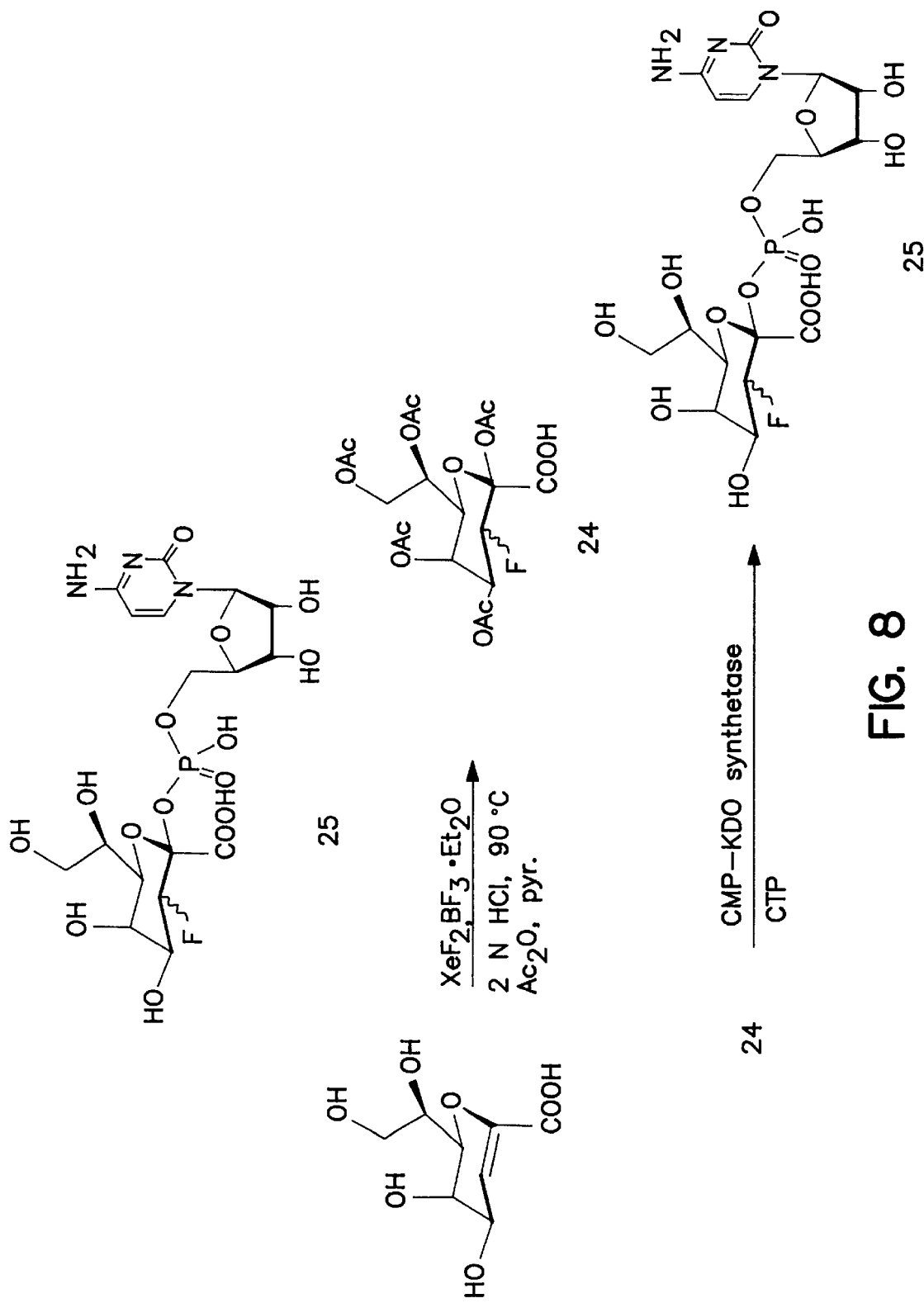
FIG. 8 illustrates the synthesis of CMP-2-fluoro-KDO (27) as an inhibitor of KDO-transferases as carried out with the indicated steps using CMP-KDO synthase to couple nucleotide with sugar.

Another novel chemoenzymatic methodology using CMP-sialic acid synthetase and CMP-KDO synthetase is employed for the synthesis of the glycosyl inhibitors cytosine-5'-monophospho-2-deoxy-2-fluoro-D-sialic acid and cytosine-5'-monophospho-2-deoxy-2-KDO (FIGS. 7 and 8) respectively. The procedure differs from the other procedures in that it does not require a phosphorylation of the glycoside. The coupling of the nucleotide to the glycoside is directly accomplished using a synthetase enzyme. First, the corresponding fucal is converted to the acetylated 1,2-difluoro compound using xenon difluoride hydrolysis (Korytnyk et al.(1982) *Tetrahedron* 38, 2547–2550) of the difluoride with hydrochloric acid the 2-fluoro-L-fucose derivative 22 and 24. The nucleotide-linked-2-deoxy-2-fluoroglycoside is then directly formed using CMP-sialic acid synthetase or CMP-KDO synthase according to conditions developed by Liu et al. (1992) *J. Am. Chem Soc.* 114, 3901–3910 (cytosine-5'-monophospho-2-deoxy-2-fluoro-D-sialic acid; FIG. 7) and Ghalambor et al. (1966) *J. Biol. Chem.* 241, 3216 (cytosine-5'-monophospho-2-deoxy-2-KDO; FIG. 8).

Chemical Methodoloay for the Synthesis of Nucleoside Diphosphate Sugars

In the chemical synthesis of nucleoside diphosphate sugars, we have demonstrated that 1H-tetrazole is an efficient catalyst for phosphoromorpholidate coupling reactions. Qualitative kinetic investigations and mass spectrometric analysis suggest a mixture of general acid catalysis and nucleophilic catalysis to be responsible for the rate acceleration. Reaction times are shorter and yields are higher than that reported previously. Since a variety of NMP-morpholidates is commercially available, the tetrazole activated coupling with glycosyl phosphates provides easy access to sugar nucleotides for subsequent glycosyltransferase catalyzed glycosylations.

Figure 12:
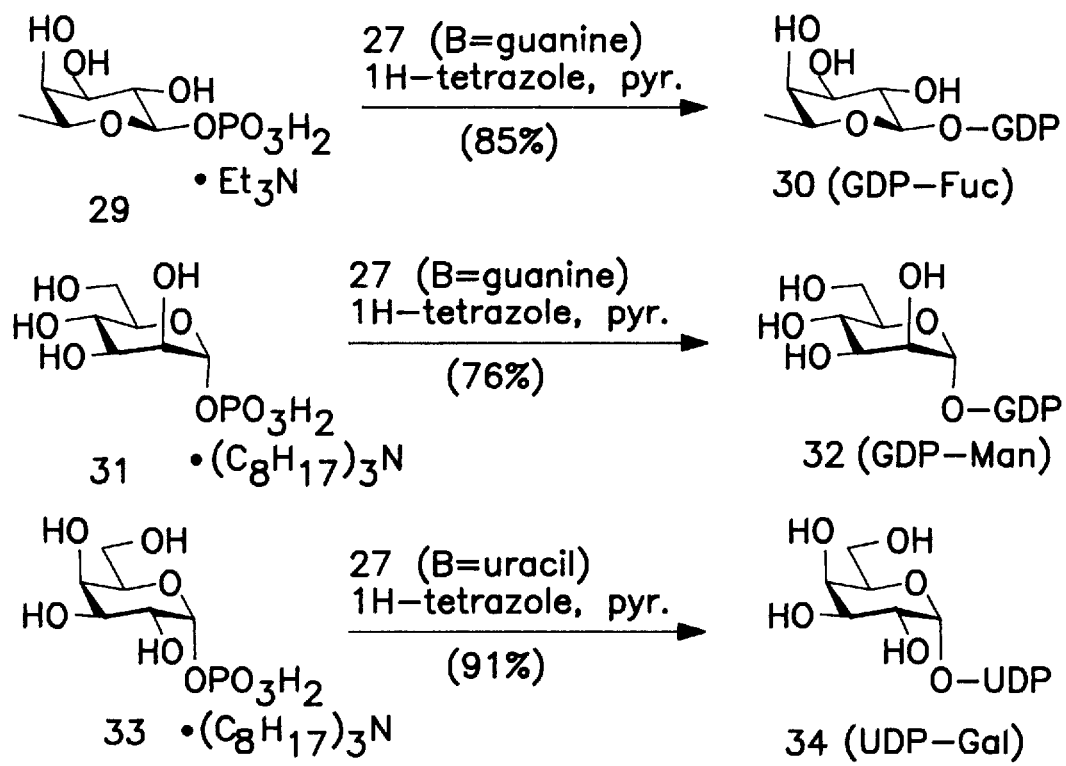
FIG. 12 illustrates the chemical strategy using tetrazole as a catalyst for the synthesis of compounds 30, 32, and 34.

The best results for the reaction of a glycosyl phosphate 26 in its trialkylammonium form and an NMP-morpholidate 27 are usually obtained if the reaction is carried out in pyridine (Moffatt et al. *J. Am. Chem. Soc.* 1958, 80, 3756–3761). However, in the case of GDP-Fuc even after a reaction time of five days we were able to detect large amounts of both starting materials, as judged by TLC. As the morpholino group in 27 has to become protonated to serve as an efficient leaving group and the trialkylammonium counterion of 26 (aqueous $pK_a$ ca. 10–11; all $pK_a$ data given orrespond to aqueous systems) is the only proton source present, we felt that the addition of an acid catalyst probably could enhance the outcome of the reaction. 1H-Tetrazole ($pK_a$ 4.9) is commonly used for the activation of phosphoramidites (Barone et al. *Nucl. Acids Res.* 1984, 12, 4051–4061; Sim et al. *J. Am. Chem. Soc.* 1993, 115, 2260–2267) and it turned out that this heterocycle is also an efficient catalyst for the phosphoramidate coupling. In this way, reaction of triethylammonium fucosyl phosphate 29 with guanosine 5'-monophospho morpholidate (27, B=guanine) (GMP-morpholidate; Sigma) and 1H-tetrazole in pyridine was complete after two days (FIG. 12). As we found, a single purification step, namely size exclusion chromatography on Bio-Gel P-2 using ammonium bicarbonate solution as eluent, gave spectroscopically pure GDP-Fuc 30. Under these conditions, an almost complete (>98%) exchange of the alkylammonium counterions occurs and 30 is obtained in 85% yield as its ammonium salt. This material turned out to be a convenient storage form and was successfully used in the fucosyltransferase catalyzed synthesis of sialyl Lewis X. In an analogous manner monotrioctylammonium mannosyl phosphate 31 and monotrioctylammonium galactosyl phosphate 33 were converted into GDP-Man 32 (Pallanca et al. *J. Chem. Soc., Perkin Trans.* 1 1993, 3017–3022) and UDP-Gal 34 (Heidlas et al. *J. Org. Chem.* 1992, 57, 152–157) in 76 and 91%, respectively.

A common problem in couplings with GMP-morpholidate is its low solubility in pyridine. Interestingly, after addition of tetrazole to a mixture of GMP-morpholidate and pyridine, a homogeneous solution is obtained immediately.

Figure 14:
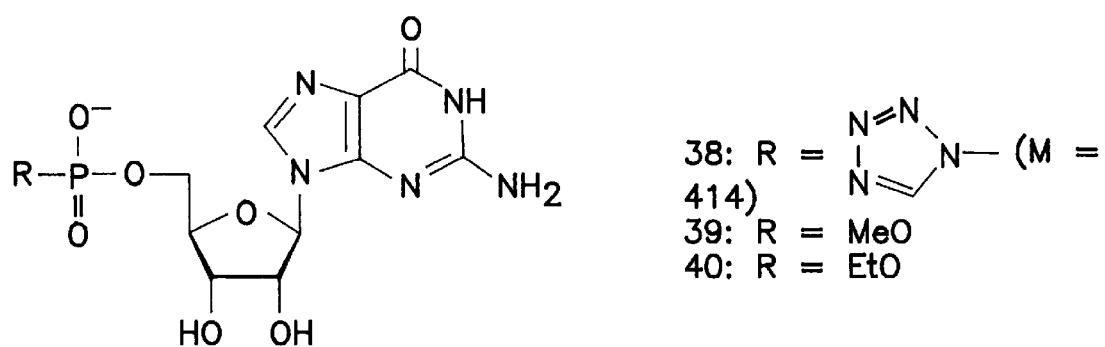
FIG. 14 illustrates phosphorotetrazolide intermediate 38 and phosphodiesters 39 and 40 which are proposed as key intermediates in the mechanism of the tetrazole catalysed chemical synthesis of the sugar diphosphate nucleosides.
Figure 15A:
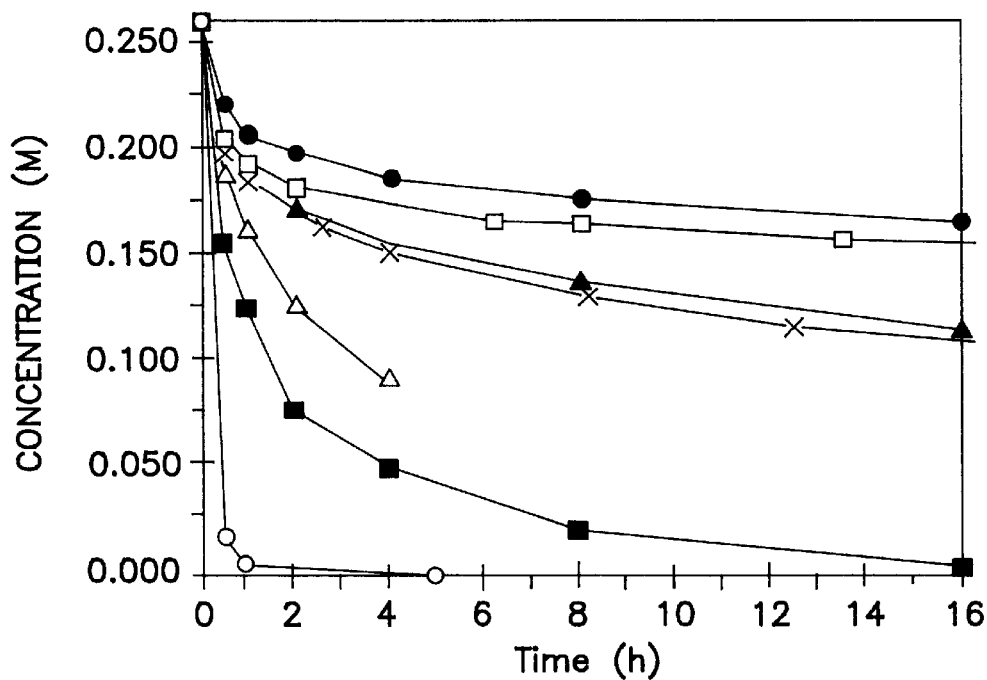
FIGS. 15A and 15B show two graph which illustrates $^1$P NMR monitoring of (A) GMP-morpholidate and (B) GDP-Fuc 30 during reaction of β-L-fucopyranosyl phosphate 29 with 1.3 equiv. of GMP-morpholidate and 3.2 equiv. of an additive in 7:3 pyridine/DMSO-d$_6$. (1) no additive; (o) 1,2,4-triazole; (s) acetic acid; (×) NHS; (Δ) DMAP.HCl; (n) 1H-tetrazole; (°) perchloric acid.
Figure 15B:
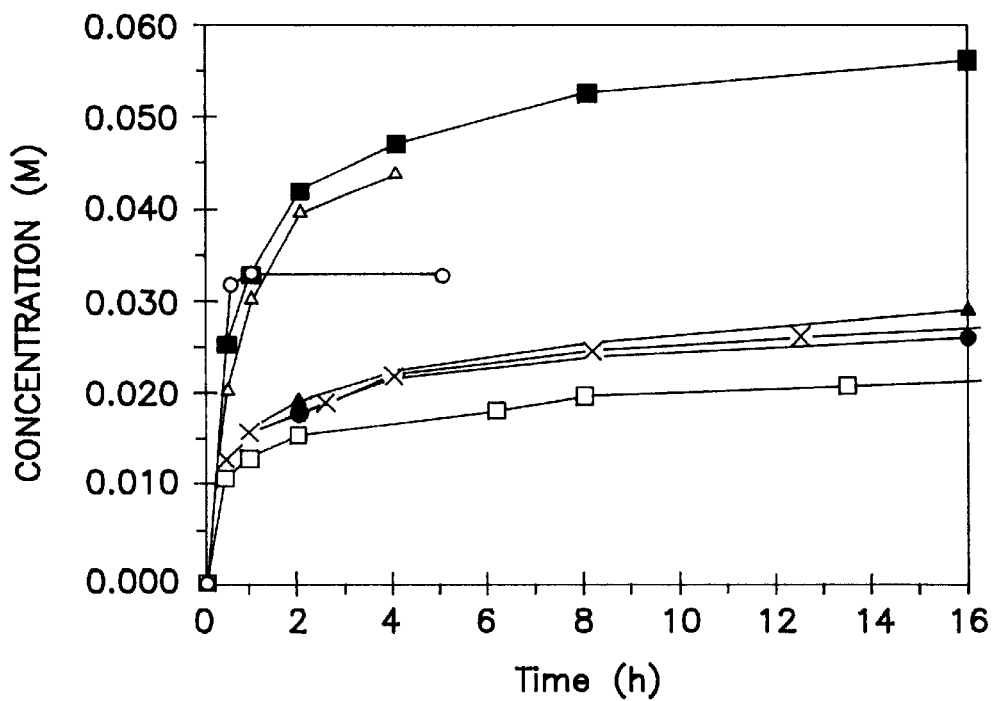

From its use in the activation of phosphoramidites it is known that tetrazole acts both as an acid and nucleophilic catalyst and tetrazolophosphane derivatives have been identified as reactive intermediates (Dahl et al. *Nucl. Acids Res.* 1987, 15, 1729–1743; Berner et al. *Nucl. Acids Res.* 1989, 17, 853–864). In order to get information about the mechanism of the tetrazole activation of phosphoromorpholidates, we carried out the coupling reaction with different additives and followed the course of the reaction by $^{31}$P NMR spectroscopy (FIG. 15). As solvent we used a 7:3 mixture of pyridine and DMSO-$d_6$ in order to prevent precipitation of GDP-Fuc or guanosine 5'-monophosphate (GMP). The additives used were 1H-tetrazole, 1,2,4-triazole, acetic acid, N-hydroxysuccinimide (NHS), 4(dimethylamino)pyridine hydrochloride (DMAP.HCl), and perchloric acid. FIG. 15A shows the decrease of GMP-morpholidate and FIG. 15B the increase of product GDP-Fuc over the time. Since the amount of hydrolysis was different in every reaction, the former gives a more realistic picture of the degree of activation of the morpholidate. Although tetrazole and acetic acid ($pK_a$ 4.75) have almost identical $pK_a$ values, tetrazole accelerates the reaction much more than acetic acid, suggesting an additional mechanism to simple acid catalysis, possibly nucleophilic catalysis. On the other hand, 1,2,4-triazole ($pK_a$10.0) has only little effect on the reaction rate compared with the uncatalyzed coupling. The addition of a nucleophile alone is obviously not sufficient, a proton source is also needed. DMAP is a widely used hypernucleophilic acylation catalyst. When applied as its hydrochloride ($pK_a$ 6.1) it is almost as effective as tetrazole but due to its restricted solubility in the reaction medium its practical importance is rather low. NHS ($pK_a$ 6.1) shows the same acceleration as acetic acid, suggesting some enhancement due to nucleophilic catalysis but it is not as efficient as the equal acidic DMAP.HCl. By far the strongest activation acid is perchloric acid. Since perchlorate is a poor nucleophile, we conclude that acid alone is sufficient for activating the morpholidate. However, beside GDP-Fuc large amounts of GMP were also formed, resulting in a lower yield of GDP-Fuc than in the case with tetrazole. From these findings, we propose that tetrazole activates GMP-morpholidate first by protonation of the leaving group nitrogen and in a second step by formation of the highly reactive phosphorotetrazolide 38 (FIG. 14). Finally, 38 reacts with fucosyl phosphate 29 to GDP-Fuc 30.

In accordance with the proposed intermediate 38 was the observation of a new resonance at a δ–12.2 ppm in a $^{31}$P NMR spectrum taken from a solution of GMP-morpholidate in pyridine/DMSO-$d_6$ (7:3) 10 min after addition of 2 equiv. of tetrazole. The integral of this signal corresponded to 4% of used morpholidate. When treated with excess of methanol or ethanol, this signal disappeared immediately and new resonances at −1.4 and −1.3 ppm, arising from the phosphodiesters 39 and 40, respectively, showed up slowly. In addition, we subjected a mixture of GMP-morpholidate and tetrazole in pyridine to mass spectrometric analysis, using electrospray ionization in the negative mode. A spectrum taken after 20 min (the mass spectrum was recorded after dilution with dioxane) showed, in addition to the peaks of starting material (M—H+431, 100%) and hydrolysis product GMP (M—H+362, 5.3%), a new peak at m/z 414 (16%) being consistent with the proposed intermediate 38. In agreement with the proposed mechanism that protonation occurs first in the activation of GMP-morpholidate is the observation that the addition of powdered 4Å molecular sieves (which react markedly as base in an aqueous suspension) strongly inhibits the coupling reaction even in the presence of tetrazole.

Synthetic Protocals

General $^1$HNMR spectra were recorded on a Bruker AMX-500 NMR spectrometer. Mass spectra were recorded on an API III PE Sciex triple-quadrupole mass spectrometer.

Water was distilled from Milli-Q water system in Millipore. Chemicals and solvents were reagent grade and were used without further purification. XeF$_2$ was purchased from Aldrich. D-Galactal was obtained from Sigma. Tri-O-acetyl-D-galactal was received from Pfanstiehl Laboratories, Inc. Ion-exchange resin (Dowex 1X8, Cl$^-$ from, 100–200 mesh) was obtained from Sigma. ATP.Na$_2$, phospho(enol)pyruvate N-salt, UTP.Na$_3$, UDP-glucose and HEPES were purchased from Sigma. Analytical thin-layer chromatography was performed with pre-coated Merck silica gel type 60, F$_{254}$.

The following enzymes were obtained from Sigma: galactokinase (from galactose-adapted yeast, EC 2.7.1.6, Sigma G0130), pyruvate kinase (from rabbit muscle, EC 2.7.1.40, Sigma P9136), galactose-1-phosphate uridyl transferase (from galactose-adapted yeast, EC 2.7.7.12, G4256), uridine-5'-diphosphoglucose pyrophposphorylase (from bakers yeast, EC 2.7.7.9, Sigma U8501), inorganic pyrophosphatase (from bakers yeast, EC 3.6.1.1, Sigma I4503). Commercial enzymes were not assayed; the reported activities refer to the activities stated by Sigma.

The enzyme-catalyzed reactions were performed in teflon tube under argon at ca. 20° C. Oxygen was removed from the solution before use by bubbling a stream of argon through the stirred solution for 30–45 min.

Anhydrous pyridine was purchased from Aldrich and used without further purification. N-Acetyllactosamine, Dowex 1-X8, MES, pyruvate kinase, lactate dehydrogenase, PEP, GDP, NADH, guanosine 5'-monophospho-morpholidate 4-morpholine-N,N'-dicyclohexylcarboxamidine salt, GDP-Fuc, and cacodylic acid were purchased from Sigma. Guanosine 5'-diphospho-[U-$^{14}$C]-b-L-fucose was purchased from Amersham Life Science. ScintiVerseI scintillation cocktail and MnCl$_2$.4 H$_2$O were purchased from Fisher Scientific Company. Protein concentrations were determined with the Coomassie protein staining reagent with albumin standards as purchased from Pierce. The scintillation counter used was the Beckman LS 3801. Fluorescence was measured on a Hitachi F2000 Fluorescence Spectrophotometer. Human a-1,3-fucosyltransferase and LacNAc-b-O—(CH$_2$)$_5$CO$_2$CH$_3$ were prepared according to published procedures (Murray et al.(1996) Biochemistry 35, 11183–11195.).

Preparation of 2-fluoro-D-galactose (5) from D-galactal (4) (FIG. 1).

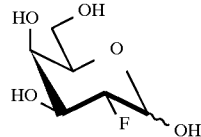

In a 30-mL round bottomed flask was placed a mixture of D-galactal (146 mg, 1.0 mmol; Aldrich), XeF$_2$ (305 mg, 1.8 mmol) and water (2.5 mL). After stirring at room temperature for 1.5 h, the solution was neutralized with K$_2$CO$_3$ and evaporated. The resulted residue was dissolved in methanol (5 mL) and the solution was filtered to remove salt. The obtained filtrate was evaporated and purified by silica gel column chromatography (1.5 cm×15 cm) with CHCl$_3$-Methanol (50:1–5:4) to give 5 (54.6 mg, 30%, α/β=1:1.5). $^1$H NMR (D$_2$O, 500 MHz) δ 5.418 (d, J=4.0 Hz, α-form, 1H), 4.789 (dd, J=7.8, 3.3 Hz, β-form, 1H), 4.613 (ddd, J=49.5, 10.0, 4.0 Hz, α-form, 1H), 4.277 (ddd, J=52.0, 9.5, 8.0 Hz, β-form, 1H), 4.08–3.86 (m), 3.72–3.67 (m). HRMS (FAB) Calcd. for C$_6$H$_{11}$O$_5$F (M+Na$^+$) 205.0488: Found 205.0482. The data are consistent with the literature values (Adamson, J.; Marcus, D. M. Carbohydr. Res. 1972, 22, 257). (The initial reaction mixture was found to be acidic (pH=1.5). Prepared as above from 1 mmol galactal and 1.8 mmol of XeF$_2$ in 2.5 mL water. After reaction, the mixture was neutralized with K$_2$CO$_3$ and evaporated, and purified by silica gel chromatography with CHCl$_3$—MeOH (50:1 to 5:4) to give compound 5 (54.6 mg, 30%))

1,2-Dideoxy-1,2-difluoro-tri-O-acetyl-D-galactose (3) (FIG. 1).

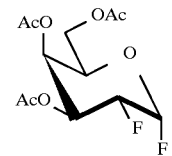

In a 50-mL round bottomed flask was placed a mixture of tri-O-acetyl-D-galactal (870 mg, 3.2 mmol; Aldrich), XeF$_2$ (540 mg, 3.2 mmol) and anhydrous diethylether (17 mL). To the mixture was added a solution of BF$_3$.OEt$_2$ (120 μL; boron trifluoride etherate is commercially available from Aldrich) in anhydrous benzene (16 mL) and stirred at room temperature for 2.5 h. The reaction mixture was washed with NaHCO$_{3aq}$ (50 mL×2) and H$_2$O (50 mL) and then the organic layer was dried over MgSO$_4$. After evaporation, the residue was purified by silica gel column chromatography with hexane-ethyl acetate (4:1) to give 3 (770 mg, 78%). $^1$H NMR (CDCl$_3$, 500 MHz) δ 5.861 (dd, J=53.0, 2.5 Hz, 1H), 5.558 (td, J=3.0, 1.3 Hz, 1H), 5.423 (td, J=11.0, 3.1 Hz, α-form, 1H), 4.793 (dddd, J=49.0, 23.5, 10.0, 3.0 Hz, 1H), 4.427 (m, 1H), 4.140 (m, 1H), 2.152 (s, 1H), 2.069 (s, 1H), 2.067 (s, 1H). HRMS (FAB) Calcd. for C$_{12}$H$_6$O$_7$F$_2$ (M+Cs$^+$) 442.9918: Found 442.9905. The data are consistent with the literature values from the sources as follows Korytnyk et al. Tetrahedron Lett. 1980, 21, 1493; Korytnyk et al. Tetrahedron 1982, 38, 2547; Tius et al. Tetrahedron 1995, 51, 6605. We have improved yield to 78% using equivalent of XeF$_2$ and catalytic BF$_3$.Et$_2$O in ether-benzene.

Preparation of 2-fluoro-D-galactose (5) from 1,2-Dideoxy-1,2-difluoro-tri-O-acetyl-D-galactose (3) (FIG. 1).

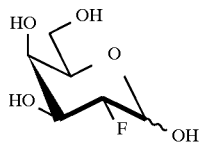

In a 30-mL round bottomed flask equipped with reflux condenser was placed a solution of galactose 3 (765 mg, 2.47 mmol) in 2N HCl (6 mL). After stirring at 90° C. for 2 h, the reaction mixture was neutralized with $K_2CO_3$ and evaporated. The residue was dissolved in Methanol(10 mL) and the solution was filtrated to remove the salt. The obtained filtrate was purified by silica gel column chromatography (1.5 cm×15 cm) with $CHCl_3MeOH$ (50:1–5:4) to give 5 (629 mg, 83%, α/β=1:1.6).

2-Deoxy-2-fluoro-α-D-Galactopyranosyl phosphate (6) (FIG. 2).

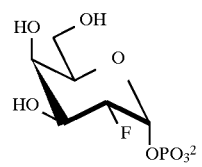

To a solution of HEPES buffer (100 mM, pH 7.49 mL) containing $MgCl_2\cdot 6H_2O$ (10 mM), $MnCl_2\cdot 4H_2O$ (5 mM), KCl (20 mM), $ATP\cdot Na_2$ (18.1 mg, 33 μmol), phospho(enol)pyruvate·$Na_3$ (111.2 mg, 0.475 mmol), cysteine (8.0 mg, 66 μmol) was added 5 (59.6 mg, 0.327 mmol), dithiothreitol (12.7 mg, 82 μmol) galactokinase (5 units) and pyruvate kinase (200 units), and the reaction mixture was then stirred at room temperature under argon. After 4 days, $BaCl_2\cdot H_2O$ (254.8 mg, 1.04 mmol; Aldrich) was added and the solution was stirred at 4° C. for 6 h. The obtained white precipitate was removed by centrifugation and the precipitate was further washed with $H_2O$ (6 mL). After the supernatant was collected, acetone (1 vol.) was added and the cloudy solution was allowed to stand for a day at 4° C. The solution was centrifuged and the collected precipitate was washed with cold $H_2O$-acetone (1:1, 5 mL×2) and acetone (5 mL). After the resulted powder was dried in vacuo, the barium salt of 6 was obtained (75 mg, 58%). An aliquot was treated with ion-exchange resin (Dowex 50W-X8, $H^+$ form) and neutralized with NaOH and evaporated for characterization. $^1H$ NMR ($D_2O$, 500 MHz) δ 5.613 (dd, J=8.3, 3.8 Hz, 1H), 4.596 (dddd, J=50.0, 10.0, 3.8, 1.8 Hz, 1H), 4.118 (m, 2H), 4.007 (m, 1H), 3.697 (m, 2H), 3.140 (m, 1H), 2.152 (s, 1H), 2.069 (s, 1H), 2.067 (s, 1H).

Uridine 5'-diphospho-2-deoxy-2-fluoro-α-D-galactose (1) (FIG. 2).

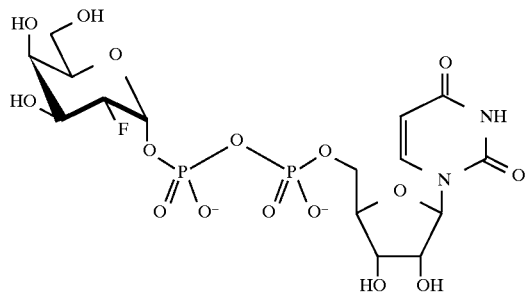

Compound 6 (70 mg, 176 μmol) was dissolved in $H_2O$ (1 mL) and treated with Dowex 50W-X8, $H^+$ form, ca. 0.7 mL) for 20 min. After filtration to remove the resin and washed with $H_2O$ (1 mL×3), the filtrate was neutralized with 1N KOH. To this solution was added $MgCl_2\cdot 6H_2O$ (14 mg, 69 μmol), $MnCl_2\cdot 4H_2O$ (6.0 mg, 30 μmol), $UTP\cdot Na_3\cdot 2H_2O$ (37 mg, 63 μmol), UDP-glucose·$Na_2$ (1.8 mg, 3.2 μmol) and the solution was adjusted to pH 8.4 with 1N KOH. After bubbling a stream of Ar into the solution for 30 min, dithiothreitol (9.3 mg, 60 μmol), galactose-1-phosphate uridyl transferase (5 units), uridine-5'-diphosphoglucose pyrophposphorylase (5 units) and inorganic pyrophosphatase (5 units) was added and the mixture (total volume=15 mL) was stirred at room temperature. After 6, 21, and 45 h, 37 mg-portions of $UTP\cdot Na_3\cdot 2H_2O$ were added, respectively, and the pH of the mixture was readjusted to 8.4 with KOH. After 3 days, the reaction was stopped by immersing the tube into a bath of boiling water for 90 sec. The resulted precipitation was removed by centrifugation and the supernatant was applied on Dowex 1-X8, (100–200 mesh, $Cl^{-\ form,}$ 1.5×25 cm) ion-exchange column. After washing the column with $H_2O$ (50 mL), the desired compound was eluted from the column in a gradient of 0.04M LiCl in 0.003N HCl and 0.4M LiCl in 0.003N HCl (1.2 L) at a LiCl concentration of ca. 0.1M. The fractions containing 1 were combined and adjusted to pH 6.0 with LiOH. After evaporation, the residue was dissolved in MeOH (4 mL) and acetone (40 mL) was further added to the solution. The obtained precipitate was collected and retreated with MeOH and acetone until the supernatant solution was free from $Cl^-$. The precipitate was dissolved in $H_2O$ and treated with ion-exchange resin (Dowex 50W-X8, $H^+$ form) and neutralized with NaOH to give 1 as sodium salt (71.8 mg, 67%). $^1H$ NMR ($D_2O$, 500 MHz) δ 7.903 (d, J=8.5 Hz, 1H), 5.935 (d, J=4.0 Hz, 1H), 5.909 (d, J=8.5 Hz, 1H), 5.757 (dd, J=7.5, 4.0 Hz, 1H), 4.633 (dddd, J=49.5, 10.0, 3.5, 3.0 Hz, 1H), 4.313 (m, 2H), 4.223 (m, 1H), 4.154 (m, 4H), 4.030 (m, 1H), 3.698 (ABq, J=12.0, 7.0 Hz, 1H), 3.657 (ABq, J=12.0, 5.0 Hz, 1H). HRMS (FAB) Calcd. for $C_{15}H_{21}N_2O_{16}FP_2Na_2$ (M+H$^+$) 613.0224: Found 613.0229.

Figure 3:
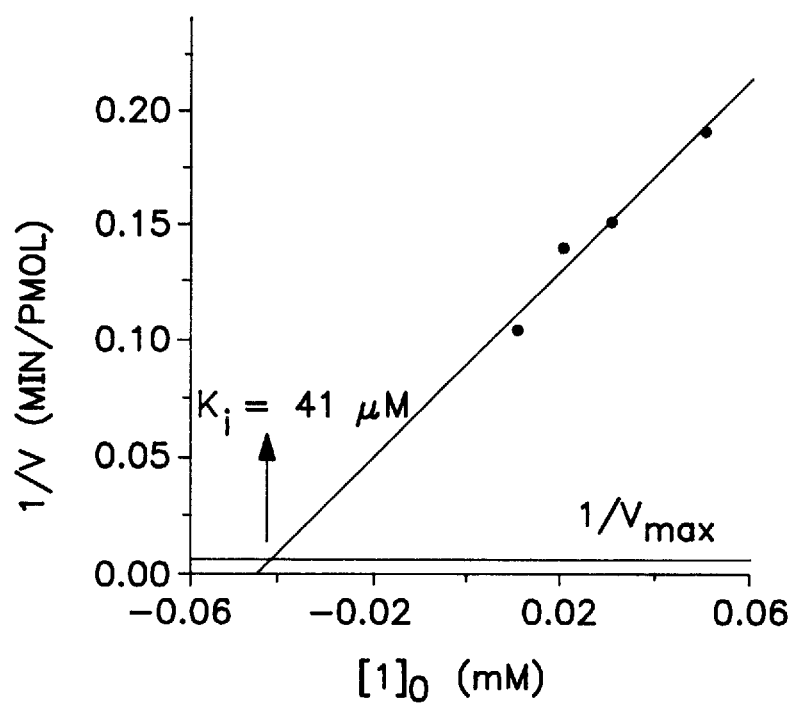
FIG. 3 illustrates shows a plot for competitive inhibition of β 1,4-galactosyltransferase with UDP-2FGal 1 in the presence of N-acetylglucosamine (GlcNAc) (1.0 mM), UDP-Gal (2.0 mM), $Mn^{2+}$(10 mM) in HEPES (100 mM, pH 7.4). The Km of GlcNAc was determined to be 5.3±0.5 mM (lit=6.0 mM, Morrison, J. F.; Ebner, K. E. *J. Biol. Chem.* 1971, 246, 3977) with $V_{max}$=0.14±0.01 μmol/min, and the $K_i$ value of 1 was determined to be 41 μM (r=0.984); v=initial velocity in min/picomoles; $K_i$=dissociation constant of the enzyme-inhibitor complex; $V_{max}$=maximum velocity of enzyme.

Inhibition study (FIG. 3).

All assays contained 10 mM of $MnCl_2$, 2 mM of UDP-[$^3H$]Gal, 5 μL of 0.125 mg/mL galactosyltransferase, 0.5–4 mM of N-acetylglucosamine, 0–0.05 mM of 1, and 100 mM of HEPES buffer (pH 7.4) in a total assay volume of 0.05 mL. Assay was performed at 25° C. Reactions were halted with the addition of 0.3 mL of distilled, de-ionized water after 10 min. The reaction mixtures were passed through a pipette column (2 cm) of Sepadex QAE A-25 with 1 mL of distilled, de-ionized water. The obtained fractions were collected in 10 mL of ScintiVerse I scintillation cocktail. A control reaction without enzyme was used to establish the background, non-enzymatic cleavage rate. A typical control reaction of 41754 cpm UDP-[$^3H$]Gal would result in 890 cpm of non-enzymatic column flow through.

Figure 4:
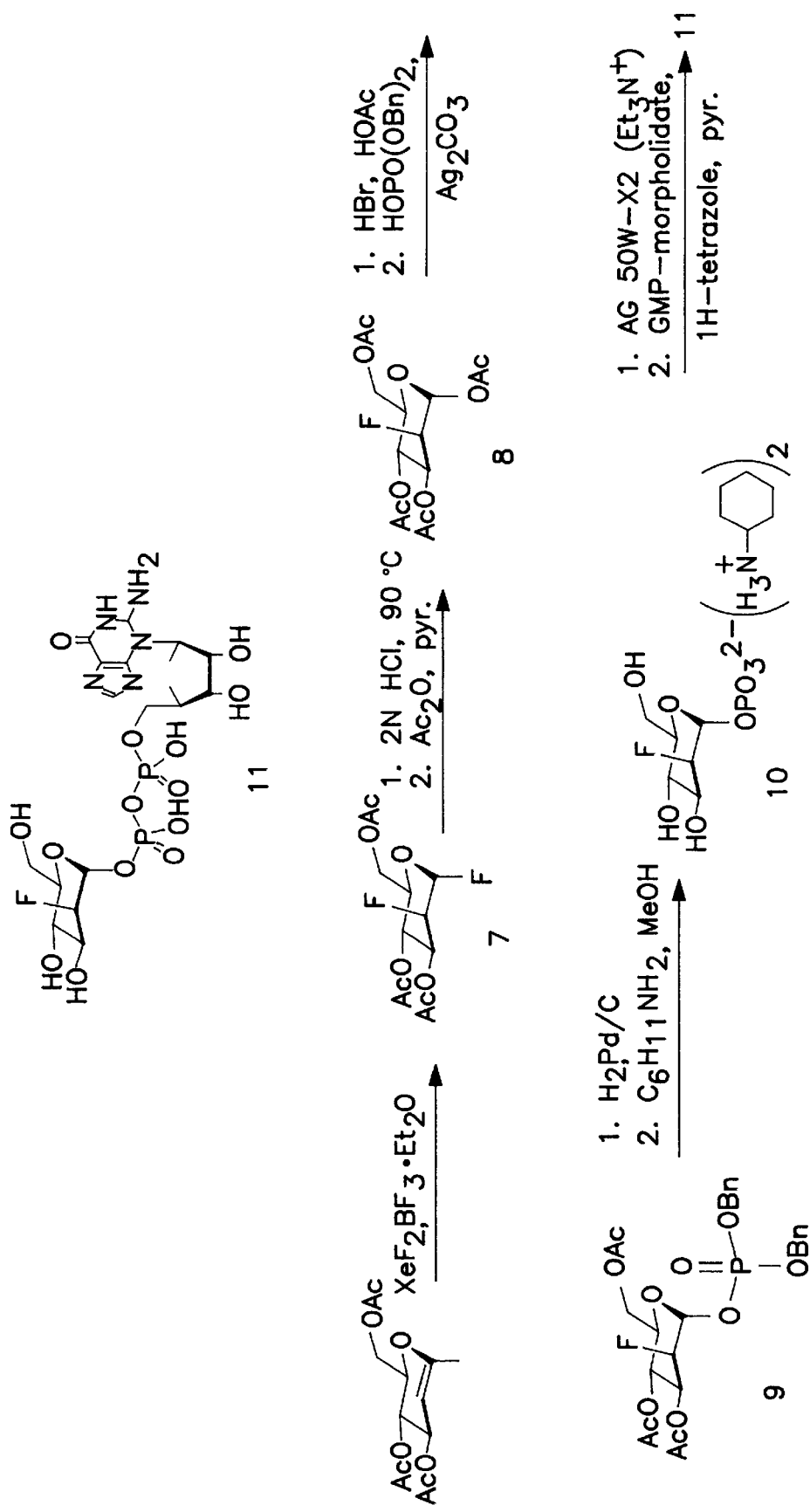
FIG. 4 illustrates the synthesis of GDP-2-deoxy-2-fluoro-D-mannose (11) as an inhibitor of a-mannosyltransferases as carried out with the indicated steps.

Preparation of GDP-2F-Man (11) from 2-deoxy-2-fluoro-D-mannose (FIG. 4)

Prepared from 3,4,6-tri-O-acetyl glucal (Aldrich) using xenon difluoride (Korytnyk et al.(1982) *Tetrahedron* 38, 2547–2550), (2.4 g, 14.5 mmol) was hydrolyzed in 2N HCl solution (15 mL) at 90° C. for 1 h. The solution was slowly cooled to 0° C., neutralized with $K_2CO_3$, and evaporated to dryness. The residue was dissolved in MeOH (30 mL) and filtered to remove salts. After evaporation, the residue was purified by silica gel chromatography (25:2 $CH_2Cl_2$—MeOH) to afford the title compound (1.80 g, 75%) as a white solid ($R_f$ 0.61, 25:2 $CH_2Cl_2$—MeOH).

Preparation of 1,3,4,6-tetra-O-acetyl-2-deoxy-2-fluoro-D-mannopyranose (8; FIG. 4).

A mixture of 2-deoxy-2-fluoro-D-mannose (1.0 g, 6.0 mmol) and $Ac_2O$ (3.4 mL, 36 mmol) in pyridine (5 mL) was stirred overnight at rt. The mixture was concentrated to an oil, which was coevaporated three times with toluene. The residue was purified by silica gel chromatography (2:1 hexane-EtOAc) to give the desired compound 8.

Preparation of 3,4,6-tri-O-acetyl-2-deoxy-2-fluoro-D-mannopyranosyl bromide (FIG. 4).

A 30% solution of HBr in HOAc (10 mL) was added dropwise into a solution of 8 (1.22 g, 4.17 mmol) in $CH_2Cl_2$ (25 mL) and $Ac_2O$ (2.5 mL) at 0° C. The solution was stirred for 2 h at 0° C., warmed to rt, and stirred an additional 1 h. The reaction mixture was poured on ice-cold water and extracted with $CH_2Cl_2$ (2×50 mL). The combined extracts were washed with sat. $Na_2CO_3$ (2×100 mL) and brine. The organic layer was dried ($MgSO_4$) and evaporated to yield the title compound (1.29 g, 99%) as a light yellow syrup used in the subsequent step without purification ($R_f$ 0.47, 2:1 hexane-EtOAc).

Preparation of (3,4,6-tri-O-acetyl-2-deoxy-2-fluoro-D-mannopyranosyl) dibenzyl phosphate (9; FIG. 4).

3,4,6-tri-O-acetyl-2-deoxy-2-fluoro-D-mannopyranosyl bromide (500 mg, 1.60 mmol), having been coevaporated twice with benzene, was dissolved in dry benzene (28 mL) and stirred with 4 Å molecular sieves for 30 min at rt. Dibenzyl phosphate (1.33 g, 4.79 mmol) and $Ag_2CO_3$ (0.88 g, 3.19 mmol) were added and the solution was stirred for 30 h in the dark. The mixture was filtered and concentrated. Silica gel chromatography (1:1 hexane-EtOAc) yielded 9 (724 mg, 89%) as a light yellow syrup ($R_f$ 0.37, 1:1 hexane-EtOAc).

Preparation of Di(cyclohexylammonium)-2-deoxy-2-fluoro-D-mannopyranosylphosphate (10; FIG. 4).

The fully protected sugar phosphate 9 (692 mg, 1.36 mmol) was dissolved in a mixture of toluene (8 mL), pyridine (1.5 mL), and $Et_3N$ (1.2 mL). 10% palladium on carbon (60 mg) was added and the solution stirred under an hydrogen atmosphere for 14 h. The mixture was filtered, evaporated, and coevaporated with toluene to yield bis(triethylammonium)-3,4,6-tri-O-acetyl-2-deoxy-2-fluoro-D-mannopyranosyl phosphate as a white foam. Crude bis(triethylammonium)-3,4,6-tri-O-acetyl-2-deoxy-2-fluoro-D-mannopyranosyl phosphate (577 mg) was dissolved in MeOH (5 mL), and cyclohexylamine (5 mL) was added, forming a precipitate. The mixture was heated to reflux for 1.5 h, during which the solution clarified, and the product finally precipitated. After 4.5 h, the mixture was cooled to rt, filtered, and the precipitate (a white solid) was washed three times with chloroform and dried (465 mg). The filtrate was evaporated to dryness, dissolved in water, washed three times with chloroform, and evaporated to yield a white solid. Recrystalization of filtrate residue from hot ethanol yielded an additional 87 mg, to give a total 552 mg (95% overall yield) of product 10.

Preparation of Guanosine 5'-diphospho-2-deoxy-2-fluoro-D-mannose, monoammonium salt (11; FIG. 4).

Compound 10 (100 mg, 235.5 mmol) was dissolved in $H_2O$ (1 mL), applied to an BioRad AG 50W-X2 cation exchange column ($Et_3N^+$, 1×10 cm), and eluted with $H_2O$ (50 mL). The solution was evaporated and coevaporated once with MeOH and three times with anhydrous pyridine (1 mL). To the dry residue guanosine 5'-monophospho morpholidate 4-morpholine-N,N'-dicyclohexylcarboxamidine salt (223 mg, 282.6 mmol) was added and the two compounds were coevaporated three times with dry pyridine (1.5 mL) keeping the flask moisture-free by using argon to bring the pressure back to normal. 1H-Tetrazole (40 mg, 565.2 mmol) and dry pyridine (1.1 mL) were added, and the solution stirred for 27.5 h at rt. The mixture was then diluted with water (1.5 mL), evaporated, and coevaporated with water two times (1.5 mL). The residue was purified with on a Bio-Gel P2 column (2.5×65 cm), eluted with 250 mM $NH_4HCO_3$ to give 11.

Preparation of UDP-2F-Glu (16) from 2-Deoxy-2-fluoro-glucose (FIG. 5):

Prepared from 3,4,6-tri-O-acetyl glucal (Aldrich) using xenon difluoride (Korytnyk et al.(1982) *Tetrahedron* 38, 2547–2550), (2.4 g, 14.5 mmol) was hydrolyzed in 2N HCl solution (15 mL) at 90° C. for 1 h. The solution was slowly cooled to 0° C., neutralized with $K_2CO_3$, and evaporated to dryness. The residue was dissolved in MeOH (30 mL) and filtered to remove salts. After evaporation, the residue was purified by silica gel chromatography (25:2 $CH_2Cl_2$—MeOH) to afford the title compound (1.80 g, 75%) as a white solid ($R_f$ 0.61, 25:2 $CH_2Cl_2$—MeOH).

Figure 5:
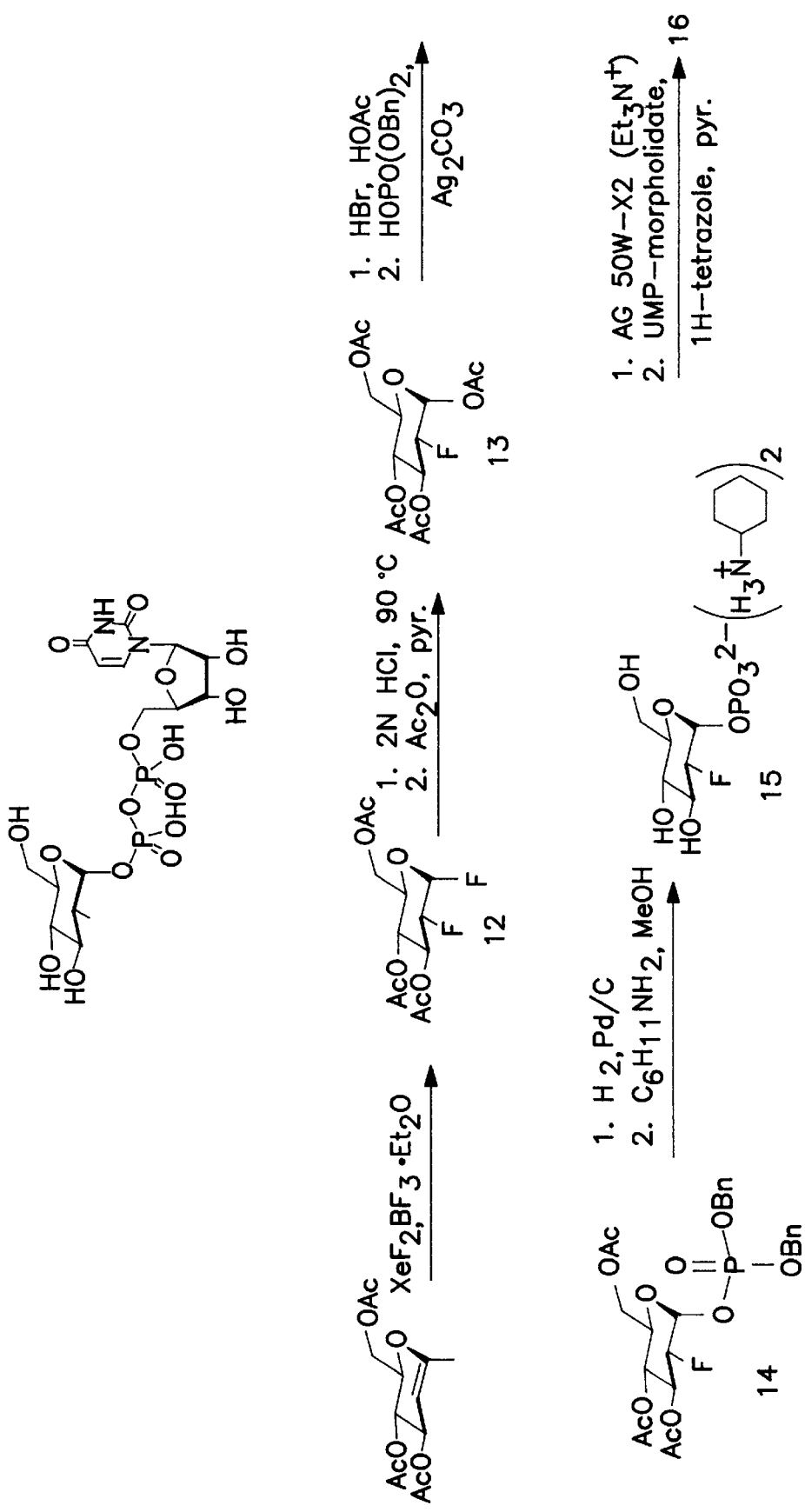
FIG. 5 illustrates the synthesis of UDP-2-deoxy-2-fluoro-D-glucose (16) as an inhibitor of glucosyltransferases and N-acetylgucosaminyltransferasesas carried out with the indicated steps.

Preparation of 1,3,4,6-tetra-O-acetyl-2-deoxy-2-fluoro-D-glucopyranose (13; FIG. 5).

A mixture of 2-deoxy-2-fluoro-D-glucose (1.0 g, 6.0 mmol) and $Ac_2O$ (3.4 mL, 36 mmol) in pyridine (5 mL) was stirred overnight at rt. The mixture was concentrated to an oil, which was coevaporated three times with toluene. The residue was purified by silica gel chromatography (2:1 hexane-EtOAc) to give 13 (1.26 g, 72%) as a colorless syrup.

Preparation of 3,4,6-tri-O-acetyl-2-deoxy-2-fluoro-D-glucopyranosyl bromide (FIG. 5).

A 30% solution of HBr in HOAc (10 mL) was added dropwise into a solution of 13 (1.22 g, 4.17 mmol) in $CH_2Cl_2$ (25 mL) and $Ac_2O$ (2.5 mL) at 0° C. The solution was stirred for 2 h at 0° C., warmed to rt, and stirred an additional 1 h. The reaction mixture was poured on ice-cold water and extracted with $CH_2Cl_2$ (2×50 mL). The combined extracts were washed with sat. $Na_2CO_3$ (2×100 mL) and brine. The organic layer was dried ($MgSO_4$) and evaporated to yield the title compound (1.29 g, 99%) as a light yellow syrup used in the subsequent step without purification ($R_f$ 0.47, 2:1 hexane-EtOAc).

Preparation of (3,4,6-tri-O-acetyl-2-deoxy-2-fluoro-D-glucopyranosyl) dibenzyl phosphate (14; FIG. 5).

3,4,6-tri-O-acetyl-2-deoxy-2-fluoro-D-glucopyranosyl bromide (500 mg, 1.60 mmol), having been coevaporated twice with benzene, was dissolved in dry benzene (28 mL) and stirred with 4 Å molecular sieves for 30 min at rt. Dibenzyl phosphate (1.33 g, 4.79 mmol) and $Ag_2CO_3$ (0.88 g, 3.19 mmol) were added and the solution was stirred for 30 h in the dark. The mixture was filtered and concentrated. Silica gel chromatography (1:1 hexane-EtOAc) yielded 14 (724 mg, 89%) as a light yellow syrup ($R_f$ 0.37, 1:1 hexane-EtOAc).

Preparation of di(cyclohexylammonium)-2-deoxy-2-fluoro-D-glucopyranosylphosphate (15; FIG. 5).

The fully protected sugar phosphate 14 (692 mg, 1.36 mmol) was dissolved in a mixture of toluene (8 mL), pyridine (1.5 mL), and $Et_3N$ (1.2 mL). 10% palladium on carbon (60 mg) was added and the solution stirred under an hydrogen atmosphere for 14 h. The mixture was filtered, evaporated, and coevaporated with toluene to yield bis(triethylammonium)-3,4,6-tri-O-acetyl-2-deoxy-2-fluoro-D-glucopyranosyl phosphate as a white foam (602 mg) Crude bis(triethylammonium)-3,4,6-tri-O-acetyl-2-deoxy-2-fluoro-D-glucopyranosyl phosphate (577 mg) was dissolved in MeOH (5 mL), and cyclohexylamine (5 mL) was added, forming a precipitate. The mixture was heated to reflux for 1.5 h, during which the solution clarified, and the product finally precipitated. After 4.5 h, the mixture was cooled to rt, filtered, and the precipitate (a white solid) was washed three times with chloroform and dried (465 mg). The filtrate was evaporated to dryness, dissolved in water, washed three times with chloroform, and evaporated to yield a white solid. Recrystalization of filtrate residue from hot ethanol yielded an additional 87 mg, to give a total 552 mg (95% overall yield) of product 15.

Preparation of Uridine 5'-diphospho-2-deoxy-2-fluoro-D-glucose (16; FIG. 5).

Compound 15 (100 mg, 235.5 mmol) was dissolved in $H_2O$ (1 mL), applied to an BioRad AG 50W-X2 cation exchange column ($Et_3N^+$, 1×10 cm), and eluted with $H_2O$ (50 mL). The solution was evaporated and coevaporated once with MeOH and three times with anhydrous pyridine (1 mL). To the dry residue guanosine 5'-monophospho morpholidate 4-morpholine-N,N'-dicyclohexylcarboxamidine salt (223 mg, 282.6 mmol) was added and the two compounds were coevaporated three times with dry pyridine (1.5 mL) keeping the flask moisture-free by using argon to bring the pressure back to normal. 1H-Tetrazole (40 mg, 565.2 mmol) and dry pyridine (1.1 mL) were added, and the solution stirred for 27.5 h at rt. The mixture was then diluted with water (1.5 mL), evaporated, and coevaporated with water two times (1.5 mL). The residue was purified with on a Bio-Gel P2 column (2.5×65 cm), eluted with 250 mM $NH_4HCO_3$ to give 16.

Figure 6:
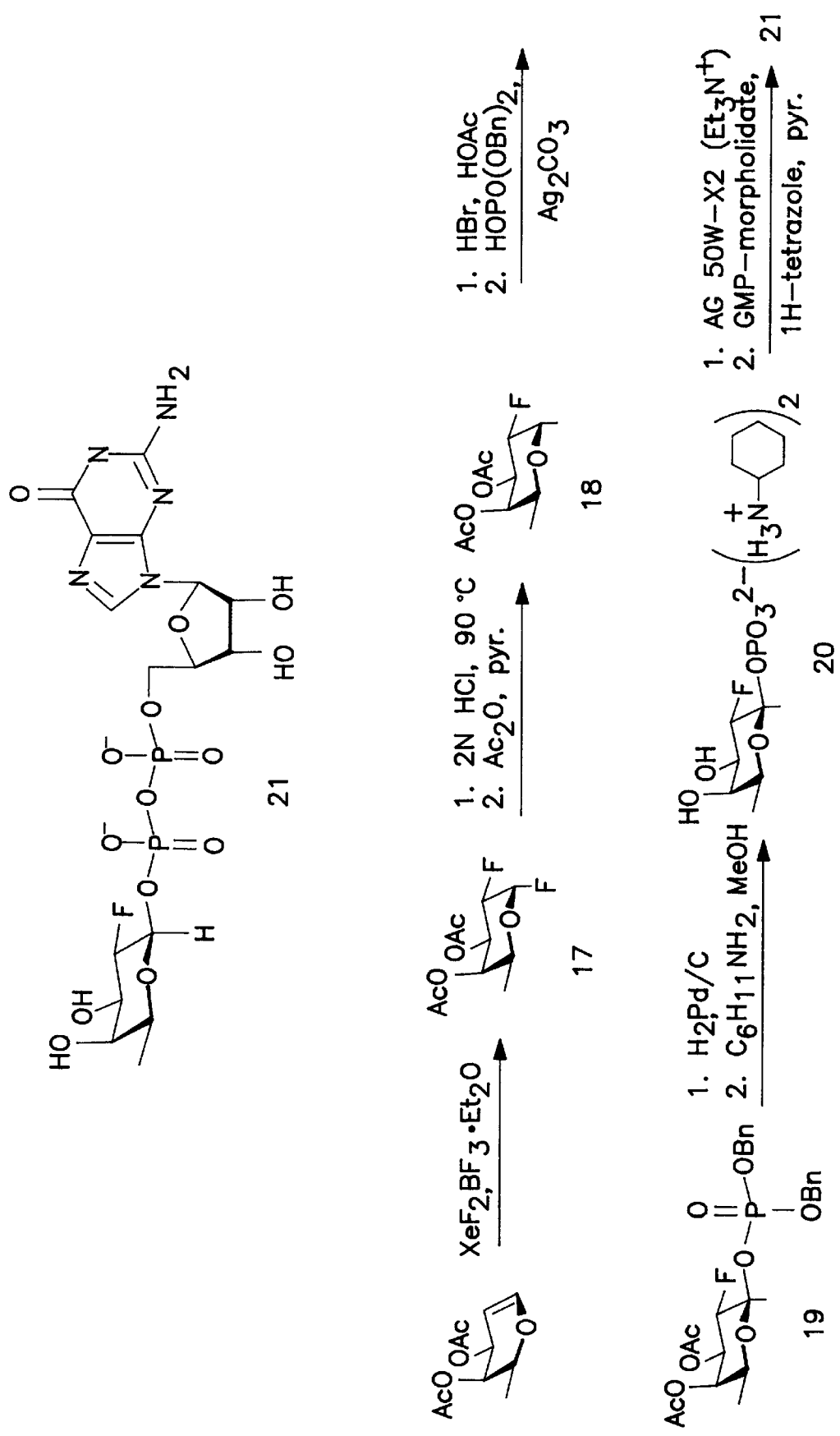
FIG. 6 illustrates the synthesis of GDP-2-deoxy-2-fluoro-L-fucose (21) as an inhibitor of α-fucosyltransferases as carried out with the indicated steps.

Preparation of GDP-2F-Fuc (21) (FIG. 6) 2-Deoxy-2-fluoro-3,4-di-O-acetyl-α-L-fucopyranosyl fluoride (FIG. 6)

Prepared from 3,4-di-O-acetyl-L-fucal (Aldrich) using xenon difluoride (Korytnyk et al.(1982) *Tetrahedron* 38, 2547-2550), (2.4 g, 14.5 mmol) was hydrolyzed in 2N HCl solution (15 mL) at 90° C. for 1 h. The solution was slowly cooled to 0° C., neutralized with $K_2CO_3$, and evaporated to dryness. The residue was dissolved in MeOH (30 mL) and filtered to remove salts. After evaporation, the residue was purified by silica gel chromatography (25:2 $CH_2Cl_2$—MeOH) to afford the title compound 17 (1.80 g, 75%) as a white solid ($R_f$ 0.61, 25:2 $CH_2Cl_2$—MeOH). $^1H$ NMR analysis of the product indicated a mixture of α and β anomers in a ratio of 1:1.7. $^1H$ NMR ($D_2O$, 500 MHz) a anomer: δ 1.16 (d, $J_{6,5}$=6.6, 3 H, H-6), 3.83 (ddd, $J_{4,5}$=1.4, $J_{4,3}$≈$J_{4,F}$≈3.7, 1 H, H-4), 4.07 (ddd, $J_{3,4}$=3.6, $J_{3,2}$=10.1, $J_{3,F}$=12.6, 1 H, H-3), 4.19 (dq, $J_{5,4}$=1.4, $J_{5,6}$=6.6, 1 H, H-5), 4.58 (ddd, $J_{2,1}$=4.0, $J_{2,3}$=10.1, $J_{2,F}$=49.8, 1 H. H-2), 5.36 (d, $J_{1,2}$=4.0, 1 H, H-1); β anomer: d 1.20 (d, $J_{6,5}$=6.5, 3 H, H-6), 3.77 (ddd, $J_{4,5}$=1.2, $J_{4,3}$≈$J_{4,F}$≈3.4, 1 H, H-4), 3.80 (dq, $J_{5,4}$=1.2, $J_{5,6}$=6.5, 1 H, H-5), 3.89 (ddd, $J_{3,4}$=3.6, $J_{3,2}$=9.5, $J_{3,F}$=14.4, 1 H, H-3), 4.25 (ddd, $J_{2,1}$=7.8, $J_{2,3}$=9.6, $J_{2,F}$=52.1, 1 H, H-2), 4.76 (dd, $J_{1,F}$=3.4, $J_{1,2}$=7.8, 1 H, H-1); $^{13}C$ NMR ($D_2O$, 120 MHz) α anomer: δ 17.75 (C-6), 70.20 (d, $J_{3,F}$=17.2, C-3), 73.58 (C-5), 74.81 (d, $J_{4,F}$=8.7, C-4), 91.34 (d, $J_{2,F}$=182.0, C-2), 92.22 (d, $J_{1,F}$=21.4, C-1); b anomer: d 17.75 (C-6), 68.80 (C-5), 73.79 (d, $J_{3,F}$=16.7, C-3), 74.41 (d, $J_{4,F}$=8.9, C-4), 94.85 (d, $J_{2,F}$=179.4, C-2), 96.21 (d $J_{1,F}$=23.5, C-1); HRMS calcd for $C_6H_{11}FNaO_4$ ($M+Na^+$) 189.0539, found 189.0534.

Preparation of 1,3,4-Tri-O-acetyl-2-deoxy-2-fluoro-L-fucopyranose (18; FIG. 6).

A mixture of 2-deoxy-2-fluoro-L-fucose (1.0 g, 6.0 mmol) and $Ac_2O$ (3.4 mL, 36 mmol) in pyridine (5 mL) was stirred overnight at rt. The mixture was concentrated to an oil, which was coevaporated three times with toluene. The residue was purified by silica gel chromatography (2:1 hexane-EtOAc) to give 18 (1.26 g, 72%) as a colorless syrup ($R_f$ 0.32, 2:1 hexane-EtOAc). $^1H$ NMR analysis showed an a/b ratio of 1.5:1. $^1H$ NMR ($CDCl_3$, 500 MHz) a anomer: δ 1.08 (d, $J_{6,5}$=6.5, 3 H, H-6), 1.99 (s, 3 H, C(O)$CH_3$), 2.10 (s, 6 H, 2 C(O)$CH_3$), 4.19 (br. q, $J_{5,6}$=6.5, 1 H, H-5), 4.82 (ddd, $J_{2,1}$=4.0, $J_{2,3}$=10.2, $J_{2,F}$=49.4, 1 H, H-2), 5.29 (br. dd, $J_{4,3}$=3.4, $J_{4,F}$=3.4, 1 H, H-4), 5.34 (ddd, $J_{3,4}$=3.4, $J_{3,2}$=10.2, $J_{3,F}$=11.1, 1 H, H-3), 6.35 (d, $J_{1,2}$=3.9, 1 H, H-1); β anomer: δ 1.15 (d, $J_{6,5}$=6.4, 3 H, H-6), 1.99 (s, 3 H, C (O) $CH_3$), 2.10 (s, 3 H, C () $CH_3$), 2.11 (s, 3 H, C(O)$CH_3$), 3.95 (br. q, J=6.4, 1 H, H-5), 4.56 (ddd, $J_{2,1}$=8.0, $J_{2,3}$=9.8, $J_{2,F}$=51.9, 1 H, H-2), 5.13 (ddd, $J_{3,4}$=3.6, $J_{3,2}$=9.8, $J_{3,F}$=13.1, 1 H, H-3), 5.23 (m, 1 H, H-4), 5.73 (dd, $J_{1,F}$=4.1, $J_{1,2}$=8.0, 1 H, H-1); $^{13}C$ NMR ($CDCl_3$ 125 MHz) α anomer: δ 15.5 (C-6), 20.3, 20.4, 20.7 (3 C(O)$CH_3$), 66.9 (C-5), 68.4 (d, $J_{3,F}$=18.6, C-3), 70.8 (d, $J_{4,F}$=7.8, C-4), 84.0 (d, $J_{2,F}$=190.5, C-2), 89.0 (d, $J_{1,F}$=22.2, C-1), 168.9, 169.9, 170.1 (3 C=O); β anomer: d 15.5 (C-6), 20.3, 20.4, 20.6 (3 C(O)$CH_3$), 70.0 (C-5), 70.4 (d, $J_{4,F}$=8.2, C-4), 71.1 (d, $J_{3,F}$=18.4, C-3), 86.7 (d, $J_{2,F}$=187.7, C-2), 91.4 (d $J_{1,F}$=24.1, C-1), 168.8, 169.6, 170.1 (3 C=O); HRMS calcd for $C_{12}H_{17}FNaO_7$ ($M+Na^+$) 315.0856, found 315.0861.

Preparation of 3,4-Di-O-acetyl-2-deoxy-2-fluoro-α-L-fucopyranosyl bromide (FIG. 6).

A 30% solution of HBr in HOAc (10 mL) was added dropwise into a solution of 18 (1.22 g, 4.17 mmol) in $CH_2Cl_2$ (25 mL) and $AC_2O$ (2.5 mL) at 0° C. The solution was stirred for 2 h at 0° C., warmed to rt, and stirred an additional 1 h. The reaction mixture was poured on ice-cold water and extracted with $CH_2Cl_2$ (2×50 mL)i. The combined extracts were washed with sat. $Na_2CO_3$ (2×100 mL) and brine. The organic layer was dried ($MgSO_4$) and evaporated to yield the title compound (1.29 g, 99%) as a light yellow syrup used in the subsequent step without purification ($R_f$0.47, 2:1 hexane-EtOAc).$^1H$ NMR analysis indicated the a anomer exclusively. $^1H$ NMR ($CDCl_3$, 500 MHz): δ 1.22 (d, $J_{6,5}$=6.5, 3 H, H-6), 2.06 (s, 3 H, C(O)$CH_3$), 2.17 (s, 3 H, C(O)$CH_3$), 4.44 (br. q, $J_{5,6}$=6.5, 1 H, H-5), 4.74 (ddd, $J_{2,1}$=4.2, $J_{2,3}$=10.0, $J_{2,F}$=50.4, 1 H, H-2), 5.38 (br. dd, $J_{4,3}$≈$J_{4,F}$≈3.4, 1 H, H-4), 5.48 (ddd, $J_{3,4}$=3.4, $J_{3,2}$=10.0, $J_{3,F}$=10.1, 1 H, H-3), 6.60 (d, $J_{1,2}$=4.2, 1 H, H-1); $^{13}C$ NMR ($CDCl_3$ 125 MHz) : d 15.4 (C-6), 20.5, 20.6 (2 C (O) $CH_3$), 69.4 (d, $J_{3,F}$=17.6, C-3), 70.0 (C-5), 70.5 (d, $J_{4,F}$=7.3, C-4), 84.3 (d, $J_{2,F}$=194.5, C-2), 87.9 (d, $J_{1,F}$=25.0, C-1), 169.8, 170.1 (2 C=O); HRMS calcd for $C_{10}H_{14}FNaO_5$ (M –Br+$Na^+$) 255.0645, found 255.0640.

Preparation of (3,4-Di-O-acetyl-2-deoxy-2-fluoro-β-L-fucopyranosyl) dibenzyl phosphate (19; FIG. 6).

3,4-Di-O-acetyl-2-deoxy-2-fluoro-α-L-fucopyranosyl bromide (500 mg, 1.60 mmol), having been coevaporated twice with benzene, was dissolved in dry benzene (28 mL) and stirred with 4 Å molecular sieves for 30 min at rt. Dibenzyl phosphate (1.33 g, 4.79 minol) and $Ag_2CO_3$ (0.88 g, 3.19 mmol) were added and the solution was stirred for 30 h in the dark. The mixture was filtered and concentrated. Silica gel chromatography (1:1 hexane-EtOAc) yielded 19 (724 mg, 89%) as a light yellow syrup ($R_f$0.37, 1:1 hexane-EtOAc). $^1H$ NMR analysis showed the b anomer predominantly (α/β=1:12). $^1H$ NMR ($CDCl_3$, 400 MHz): δ 1.20 (d, $J_{6,5}$=6.4, 3 H, H-6), 2.06 (s, 3 H, C(O)$CH_3$), 2.17 (s, 3 H, C(O)$CH_3$), 3.93 (dq, $J_{5,4}$=1.1, $J_{5,6}$=6.4, 1 H, H-5), 4.61 (ddd, $J_{2,1}$=7.7, $J_{2,3}$=9.9, $J_{2,2F}$=51.7, 1 H, H-2), 5.06–5.16 (m, 5 H, H-32 $CH_2Ph$), 5.28 (ddd, $J_{4,5}$=1.1, $J_{4,3}$≈$J_{4,F}$≈3.2, 1 H, H-4), 5.38 (ddd, $J_{1,F}$=3.9, $J_{1,P}$=7.3, $J_{1,2}$=7.7, 1 H, H-1), 7.30–7.38 (m, 10 H, 2 $C_6H_5$); $^{13}C$ NMR ($CDCl_3$, 100 MHz): δ 15.7 (C-6), 20.50, 20.54 (2 C(O)$CH_3$), 69.48, 69.54, 69.6, 70.2, 70.3, 70.4 (C-4, C-5), 71.0 (d, $J_{3,F}$=18.5, C-3), 87.8 (dd, $J_{2,P}$=9.2, $J_{2,F}$=188.8, C-2), 96.3 (dd, $J_{1,P}$=4.7, $J_{1,F}$=23.9, C-1), 127.83, 127.86, 127.92, 127.99, 128.47, 128.51, 128.56, 128.59 (10 C, arom.), 135.27, 135.34, 135.38, 135.46 (2 d, 2 C, quart. arom.), 169.8, 170.2 (2 C=O); $^{19}F$ NMR ($CDCl_3$): d −171.2; $^{31}P$ NMR ($CDCl_3$): d −2.19; HRMS calcd for $C_{24}H_{28}CsFO_9P$ ($M+Cs^+$) 643.0509, found 643.0539.

Preparation of Di(cyclohexylammonium)-2-deoxy-2-fluoro-α-L-fucopyranosylphosphate (20; FIG. 6).

The fully protected sugar phosphate 19 (692 mg, 1.36 mmol) was dissolved in a mixture of toluene (8 mL), pyridine (1.5 mL), and Et$_3$N (1.2 mL). 10% palladium on carbon (60 mg) was added and the solution stirred under an hydrogen atmosphere for 14 h. The mixture was filtered, evaporated, and coevaporated with toluene to yield bis (triethylammonium) -3,4-di-O-acetyl-2-deoxy-2-fluoro-b-L-fucopyranosyl phosphate as a white foam (602 mg) (R$_f$0.57, 2:1 i-PrOH-1M NH$_4$OAc). $^1$H NMR (CDCl$_3$, 400 MHz): δ 1.18 (d, J$_{6,5}$=6.3, 3 H, H-6), 2.05 (s, 3 H, C(O)CH$_3$), 2.14 (s, 3 H, C(O)CH$_3$), 3.98 (br. q, J$_{5,6}$=6.4, 1 H, H-5), 4.48 (ddd, J$_{2,1}$=7.8, J$_{2,3}$=9.7, J$_{2,F}$=51.9, 1 H, H-2), 5.14 (ddd, J$_{3,4}$≈3.5, J$_{3,2}$≈9.9, J$_{3,F}$≈13.1, 1 H, H-3), 5.24 (m, 1 H, H-4), 5.30 (ddd, J$_{1,F}$≈3.5, J$_{1,2}$≈7.8, J$_{1,P}$≈7.9, 1 H, H-1); $^{13}$C NMR (CDCl$_{3100}$ MHz): δ 15.9 (C-6), 20.5, 20.6 (2 C(O)CH$_3$), 69.2 (C-5), 71.1 (d, J$_{4,F}$=8.2, C-4), 71.4 (d, J$_{3,F}$=18.6, C-3), 88.6 (dd, J$_{2,P}$=8.1, J$_{2,F}$=185.8, C-2), 95.4 (dd, J$_{1,P}$=4.3, J$_{1,F}$=22.8, C-1), 169.9, 170.5 (2 C=O); HRMS calcd for C$_{10}$H$_{16}$FNaO$_9$P (M+Na$^+$) 353.0414, found 353.0420. Crude bis (triethylammonium) -3,4-di-O-acetyl-2-deoxy-2-fluoro-b-Lfucopyranosyl phosphate (577 mg) was dissolved in MeOH (5 mL), and cyclohexylamine (5 mL) was added, forming a precipitate. The mixture was heated to reflux for 1.5 h, during which the solution clarified, and the product finally precipitated. After 4.5 h, the mixture was cooled to rt, filtered, and the precipitate (a white solid) was washed three times with chloroform and dried (465 mg). The filtrate was evaporated to dryness, dissolved in water, washed three times with chloroform, and evaporated to yield a white solid. Recrystalization of filtrate residue from hot ethanol yielded an additional 87 mg, to give a total 552 mg (95% overall yield) of product 20. $^1$H NMR (D$_2$O, 400 Hz): δ 1.15 (m, 2 H, cha), 1.23 (d, J$_{6,5}$=6.5, 3 H, H-6), 1.31 (m, 8 H, cha), 1.63 (m, 2 H, cha), 1.78 (m, 4 H, cha), 1.95 (m, 4 H, cha), 3.12 (m, 2 H, cha), 3.78 (m, 1 H, cha), 3.82 (br. q, J$_{5,6}$=6.5, 1 H, H-5), 3.93 (ddd, J$_{3,4}$=3.7, J$_{3,2}$=9.6, J$_{3,F}$=14.2, 1 H, H-3), 4.27 (ddd, J$_{2,1}$=7.8, J$_{2,3}$=9.5, J$_{2,F}$=51.8, 1 H, H-2), 5.01 (ddd, J$_{1,F}$=3.5, J$_{1,2}$=7.8, J$_{1,P}$=8.4, 1 H, H-1); $^{13}$C NMR (D$_2$O, 100 MHz): d 17.7 (C-6), 26.2, 26.7, 32.8, 52.8 (cha), 73.5 (C-5), 73.9 (d, J$_{3,F}$=17.4, C-3), 74.4 (d, J$_{4,F}$=8.8, C-4), 94.4 (dd, J$_{2,P}$=6.8, J$_{2,F}$=181.3, C-2), 97.3 (dd, J$_{1,P}$=4.2, J$_{1,F}$=23.2, C-1); HRMS calcd for C$_6$H$_{12}$FNaO$_7$P (M+Na,) 269.0202, found 269.0197.

Preparation of Guanosine 5'-diphospho-2-deoxy-2-fluoro-β-L-fucose (21; FIG. 6).

Compound 20 (100 mg, 235.5 mmol) was dissolved in H$_2$O (1 mL), applied to an BioRad AG 50W-X2 cation exchange column (Et$_3$N$^+$, 1×10 cm), and eluted with H$_2$O (50 mL). The solution was evaporated and coevaporated once with MeOH and three times with anhydrous pyridine (1 mL). To the dry residue guanosine 5'-monophospho morpholidate 4-morpholine-N, N'-dicyclohexylcarboxamidine salt (223 mg, 282.6 mmol) was added and the two compounds were coevaporated three times with dry pyridine (1.5 mL) keeping the flask moisture-free by using argon to bring the pressure back to normal. 1H-Tetrazole (40 mg, 565.2 mmol) and dry pyridine (1.1 mL) were added, and the solution stirred for 27.5 h at rt. The mixture was then diluted with water (1.5 mL), evaporated, and coevaporated with water two times (1.5 mL). The residue was purified with on a Bio-Gel P2 column (2.5×65 cm), eluted with 250 mM NH$_4$HCO$_3$ to give 21 (106.1 mg, 74%) as a white solid after lyophilization (R$_f$0.38, 2:1 i-PrOH-1M NH$_4$OAc). $^1$H NMR (CDCl$_3$, 500 MHz): δ 1.19 (d, J$_{6,5}$=6.5, 3 H, H-6 Fuc), 3.75 (br. dd, J$_{4,3}$≈J$_{4,F}$≈3.4, 1 H, H-4 Fuc), 3.78 (br. q, J$_{5,6}$=6.5, 1 H, H-5 Fuc), 3.88 (ddd, J$_{3,4}$=3.7, J$_{3,2}$=9.7, J$_{3,F}$=14.3, 1 H, H-3 Fuc), 4.19 (m, 2 H, H-5 Rib), 4.32 (m, 1 H, H-4 Rib), 4.33 (ddd, J$_{2,1}$=7.6, J$_{2,3}$=9.8, J$_{2,F}$=51.8, 1 H, H-2 Fuc), 4.49 (dd, J$_{3,4}$=3.5, J$_{3,2}$=5.1, 1 H, H-3 Rib), 4.75 (dd, J$_{2,3}$=5.1, J$_{2,1}$=6.0, 1 H, H-2 Rib), 5.14 (ddd, J$_{1,F}$=3.7, J$_{1,2}$=7.6, J$_{1,P}$=8.0, 1 H, H-1 Fuc), 5.90 (d, J$_{1,2}$=6.01 H, H-1 Rib), 8.17 (s, 1 H, H-8, base); $^{13}$C NMR (CDCl$_3$, 125 MHz): δ 16.24 (C-6 Fuc), 66.26 (d, J=5.1), 71.42, 72.28 (d, J=16.8), 72.73, 72.78, 74.74, 84.91 (d, J=8.8), 88.11, 92.58 (dd, J$_{C,P}$=7.6, J$_{C,F}$=181.9, C-2"), 96.50 (dd, J$_{C,P}$=4.7, J$_{C,F}$=24.2, C-1"), 116.52, 138.54, 152.66, 155.10, 159.63; $^{19}$F NMR (D$_2$O): d −171.3; $^{31}$P NMR (D$_2$O): d −10.83 (d, J$_{P,P}$=19.1), −12.66 (d, J$_{P,P}$=19.1); HRMS calcd for C$_{16}$H$_{24}$FN$_5$O$_{14}$P$_2$ (M+H$^+$) 592.0857, found 592.0870.

Inhibition of FucT by GDP-2F-Fuc

GDP-Fuc concentration was varied (10, 25, 50, 100 mM) at fixed concentrations of GDP-2F-Fuc (0, 20, 40, 80 mM), and the acceptor sugar, LacNAc-b-O-(CH$_2$)$_5$CO$_2$CH$_3$, was kept at twice its K$_m$ level, 0.6 mM. Each assay contained 0.3 munit of FucT V and 10 mM MnCl$_2$ in a 100 mM MES buffer (pH 6.0). Reactions were 30 minutes at room temperature. The precise K$_i$ was determined with a nonlinear, least squares fit of the data to the equation for competitive inhibition (FIG. 9).

Evidence that GDP-2F-Fuc was not a slow substrate or an inactivator was obtained. A 0.350 mL solution that contained 10 mM MnCl2 , 2.1 munits FucT V, 0.30 mM LacNAc-b-O—(CH$_2$)$_5$CO$_2$CH$_3$, 0.010 mM GDP-2F-Fuc, and 100 mM MES (pH 6.0). This solution was subject to incubation at room temperature for various time periods (0, 3, 10, 20, 30, 60, 80 min). After the incubation time, a 0.050 mL aliquot was removed and GDP-[U-$^{14}$C]-fucose was added to a final concentration of 0.050 mM to initiate the fucosyltransfer reaction. After a 30 minute reaction time period, the solution was passed through a Dowex 1 column and the amount of product determined. A control reaction was performed that did not contain GDP-2F-Fuc which was used in the calculation of percent inhibition.

Preparation of CMP-2F-Sialic acid (23) (FIG. 7)

CMP-sialic acid synthetase is employed for the synthesis of the glycosyl inhibitor cytosine-5'-monophospho-2-deoxy-2-fluoro-D-sialic acid (FIG. 7). The corresponding fucal is converted to the acetylated 1,2-difluoro compound using xenon difluoride (Korytnyk et al.(1982) Tetrahedron 38, 2547–2550). Hydrolysis of the difluoride with hydrochloric acid gives the 2-fluoro-L-fucose derivative 22 (conditions identical as that for GDP-2F-Fuc (supra)). The nucleotide-linked-2-deoxy-2-fluoroglycoside is then formed using CMP-sialic acid synthetase according to conditions developed by Liu et al. (1992) J. Am. Chem Soc. 114, 3901–3910 (cytosine-5'monophospho-2-deoxy-2-fluoro-D-sialic acid, compound 23; FIG. 7).

Preparation of CMP-2F-KDO (25) (FIG. 8)

CMP-KDO synthetase is employed for the synthesis of cytosine-5'-monophospho-2-deoxy-2-KDO (FIG. 8). Using identical procedures illustrated supra, the corresponding fucal is converted to the acetylated 1,2-difluoro compound using xenon difluoride (Korytnyk et al.(1982) Tetrahedron 38, 2547–2550). Hydrolysis of the difluoride with hydrochloric acid gives the 2-fluoro-L-fucose derivative 24. The nucleotide-linked-2-deoxy-2-fluoroglycoside is then formed using CMP-KDO synthetase according to conditions developed by Ghalambor et al. (1966) J. Biol. Chem. 241, 3216 (cytosine-5'-monophospho-2-deoxy-2-KDO, compound 25; FIG. 8).

General preparation of 2-fluoro-glycoside from glycal.

In a 30-mL round bottomed flask was placed a mixture of sugar glycal (1.0 mmol), XeF$_2$ (1.8 mmol) and water (0.40

Molar). After stirring at room temperature for 1.5 h, the solution was neutralized with $K_2CO_3$ and evaporated. The resulted residue was dissolved in methanol (5 mL) and the solution was filtered to remove salt. The obtained filtrate was evaporated and purified by silica gel column chromatography (1.5 cm×15 cm) with $CHCl_3$-Methanol (50:1-5:4) to give 2-fluro-glycoside.

General preparation of 2-Deoxy-2-fluoro-glycosyl-pyranosyl phosphate.

To a solution of HEPES buffer (100 mM, pH 7.4) containing $MgCl_2.6H_2O$ (10 mM), $MnCl_2.4H_2O$ (5 mM), KCl (20 mM), $ATP.Na_2$ (33 μmol), phospho(enol)pyruvate.$Na_3$ (0.475 mmol), cysteine (66 μmol) is added 2-fluro-sugar (0.327 mmol; synthesized supra), dithiothreitol (82 μmol) sugar-kinase (5 units) and pyruvate kinase (200 units), and the reaction mixture is then stirred at room temperature under argon. After 4 days, $BaCl_2.H_2O$ (1.04 mmol; Aldrich) is added and the solution is stirred at 4° C. for 6 h. The obtained white precipitate is removed by centrifugation and the precipitate is further washed with $H_2O$ (6 mL on 60 mg scale) After the supernatant is collected, acetone (1 vol.) is added and the cloudy solution is allowed to stand for a day at 4° C. The solution is centrifuged and the collected precipitate was washed with cold $H_2O$-acetone (1:1, 5 mL×2 on 60 mg scale) and acetone (5 mL on 60 mg scale). After the resulted powder was dried in vacuo, the barium salt of 2-deoxy-2-fluoro-glycosyl-pyranosyl phosphate is obtained. An aliquot is treated with ionexchange resin (Dowex 50W-X8, $H^+$ form) and neutralized with NaOH and evaporated for characterization.

General Preparation of transferase inhibitor nucleotide-5'-di(mono)phospho-2-deoxy-2-fluoroglycoside.

2-deoxy-2-fluoro-sugar-pyranosyl phosphate (176 μmol; synthesized supra) is dissolved in $H_2O$ (0.176 Molar) and treated with Dowex 50W-X8, $H^+$ form, ca. (0.25 Molar) for 20 min. After filtration to remove the resin and washing with $H_2O$ (0.176 Molar amount×3), the filtrate is neutralized with 1N KOH. To this solution is added $MgCl_2.6H_2O$ (69 μmol), $MnCl_2.4H_2O$ (30 μmol), $NTP.Na_3.2H_2O$ (63 μmol; Sigma; N=any nucleotide), NMP-glucose.$Na_2$ (3.2 μmol; Sigma; N=any nucleotide) and the solution is adjusted to pH 8.4 with 1N KOH. After bubbling a stream of Ar into the solution for 30 min, dithiothreitol (60 μmol), a sugar-1-phosphate nucleotide transferase (5 units; sugar=galactose, glucose, mannose, fucose, sialic acid, KDO, etc.; a commercially available transferase), nucleotide-5'-diphosphoglucose pyrophosphorylase (5 units; Sigma) and inorganic pyrophosphatase (5 units) is added and the mixture (total volume=11.73 mMolar) is stirred at room temperature. After 6, 21, and 45 h, 37 mg-portions of $NTP.Na_3.2H_2O$ (N=any nucleotide) are added, respectively, and the pH of the mixture is readjusted to 8.4 with KOH. After 3 days, the reaction is stopped by immersing the tube into a bath of boiling water for 90 sec. The resulted precipitation is removed by centrifugation and the supernatant is applied on Dowex 1-X8, (100–200 mesh, $Cl^-$ form, 1.5×25 cm) ion-exchange column. After washing the column with $H_2O$ (50 mL on a 70 mg scale), the desired compound is eluted from the column in a gradient of 0.04M LiCl in 0.003N HCl and 0.4M LiCl in 0.003N HCl at a LiCl concentration of ca. 0.1M. The fractions containing product are combined and adjusted to pH 6.0 with LiOH. After evaporation, the residue is dissolved in MeOH (4 mL on a 70 mg scale starting material) and acetone (40 mL on a 70 mg scale) is further added to the solution. The obtained precipitate is collected and retreated with MeOH and acetone until the supernatant solution is free from $Cl^-$. The precipitate is dissolved in $H_2O$ and treated with ion-exchange resin (Dowex 50W-X8, $H^+$ form) and neutralized with NaOH to give corresponding nucleotide-linked-2-deoxy-2-fluoroglycoside as sodium salt.

Figure 13:
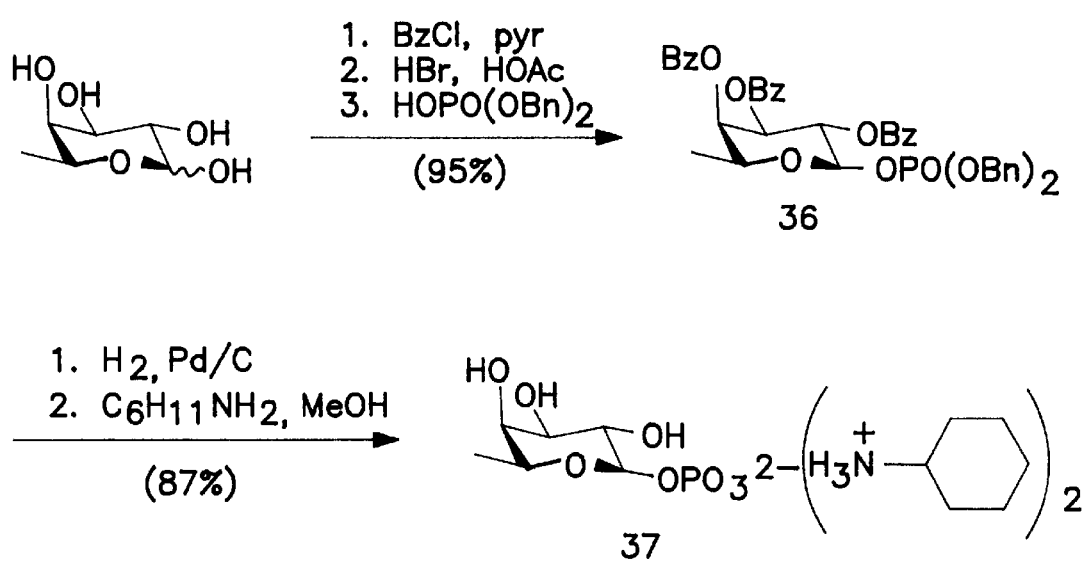
FIG. 13 illustrates the chemical strategy for the synthesis of the glycosyl phophate as its dicyclohexylammonium salt 37.

General for chemical synthesis of nucleoside diphoshate sugars:

Anhydrous pyridine was purchased from Aldrich and used without further purification. Guanosine 5'-monophospho morpholidate 4-morpholine-N,N'-dicyclohexylcarboxamidine salt, uridine 5'-monophospho morpholidate 4-morpholine-N,N'-dicyclohexylcarboxamidine salt, dipotassium α-D-mannosyl phosphate and dipotassium α-D-galactosyl phosphate were purchased from Sigma. Di(cyclohexylammonium) β-L-fucopyranosyl phosphate 39 was prepared from L-fucose in five steps and an overall yield of 82% according to published procedures (Ichikawa et al. J. Org. Chem. 1992, 57, 2943–2946; Adelhorst et al. Carbohydr. Res. 1993, 242, 69–76) (FIG. 13). Cation exchange resin AG 50W-X2 ($H^+$ form, strongly acidic) was purchased from Bio-Rad Laboratories and converted to the appropriate salt form prior to its use. When samples were coevaporated with dry pyridine in order to remove residual water, argon was used to bring the pressure back to normal. Analytical thin layer chromatography was performed using silica gel 60 $F_{254}$ pre-coated glass plates (Merck) and visualized by quenching of fluorescence and by charring after treatment with cerium molybdophoshate. Size exclusion chromatography was performed on Bio-Gel P-2 Gel, fine (Bio-Rad Laboratories). $^{31}P$ NMR spectra were recorded at 162.0 MHz (Bruker AMX-400) and referenced to internal triphenylphosphine oxide ($\delta_P$=26.5 in 7:3 pyridine/DMSO-$d_6$) which itself was referenced to 85% $H_3PO_4$ ($\delta_P$=0.00) as external standard.

Synthesis of Monoammonium guanosine 5'-diphospho-β-L-fucose (30) as illustrated in FIG. 12.

Compound 26 (624 mg, 1.41 mmol; wherein R, R'=OH; Sigma) was dissolved in $H_2O$ (15 mL), applied to a Bio-Rad AG 50W-X2 cation exchange column ($Et_3N^+$, 2.5×8 cm), and eluted with $H_2O$ (150 mL). The solution was evaporated, coevaporated with MeOH (2×10 mL) and dried for 3 d under vacuum to give triethylammonium β-L-fucopyranosyl phosphate 29 (512 mg). The content of triethylamine was determined to be 1.16 equiv. ($^1H$ NMR) A mixture of 29 (57.5 mg, 159 μmol) and guanosine 5'-monophospho morpholidate 4-morpholine-N,N'-dicyclohexylcarboxamidine salt 27 (201 mg, 255 μmol) was coevaporated with dry pyridine (3×1.5 mL). 1H-Tetrazole (33 mg, 477 μmol) and dry pyridine (0.8 mL) were added, and the solution stirred at rt. After a while, product starts to precipitate. The reaction was monitored by TLC (2:1 i-PrOH/1M $NH_4OAc$). After 2 d, the mixture was diluted with water (1.5 mL) to become a clear solution, evaporated, and coevaporated with water (2×1.5 mL). The residue was purified on a Bio-Gel P-2 column (2.5×70 cm), eluated with 250 mM $NH_4HCO_3$ to give 30 (82.4 mg, 85%) as a white solid after lyophilization ($R_f$ 0.43, 2:1 i-PrOH/1M $NH_4OAc$). The $^1H$ NMR spectral data were in agreement with the published ones (Nunez et al. Can. J. Chem. 1981, 59, 2086–2095; Gokhale et al. Can. J. Chem. 1990, 68, 1063–1071).

Synthesis of monoammonium guanosine 5'-diphospho-α-D-mannose (32) as illustrated in FIG. 12.

Dipotassium α-D-mannosyl phosphate (110 mg, 311 μmol; Sigma) was dissolved in $H_2O$ (1 mL) and passed through a Bio-Rad AG 50W-X2 cation exchange column (pyridinium form, 1.5×5 cm). The solution was concentrated to a volume of 5 mL and pyridine (15 mL) and tri-n-octylamine (136 μL, 311 μmol) were added. The mixture was evaporated and coevaporated with dry pyridine (3×1.5 mL).

Guanosine 5'-monophospho morpholidate 4-morpholine-N,N'-dicyclohexylcarboxamidine salt (392 mg, 497 μmol) was added and the mixture was coevaporated with dry pyridine (3×1.5 mL). 1H-Tetrazole (70 mg, 994 μmol) and dry pyridine (1.55 mL) were added, and the solution stirred at rt. The reaction was monitored by TLC (2:1 i-PrOH/1M $NH_4OAC$). After 2 d, the mixture was diluted with water (2 mL) and evaporated. The residue was suspended in 100 mM $NH_4HCO_3$ and extracted with ether to remove the trioctylamine. After evaporation, the residue was purified on a Bio-Gel P-2 column (2.5×95 cm), eluated with 250 mM $NH_4HCO_3$, and precipitated from $H_2O$/MeOH/acetone to give 32 (147 mg, 76%) as a white solid after lyophilization ($R_f$ 0.31, 2:1 i-PrOH/1M $NH_4OAc$). The $^1H$ NMR spectral data were in agreement with the published ones (Pallanca et al. *J. Chem. Soc., Perkin Trans.* 1 1993, 3017–3022).

Synthesis of monoammonium uridine 5'-diphospho-α-D-galactose (34) as illustrated in FIG. 12.

Dipotassium α-D-galactosyl phosphate (1.0 equivalents, Sigma), containing 5.5 mol $H_2O$, (110 mg, 253 μmol) was converted into the trioctylammonium salt using 110 μL (253 μmol) trioctylamine and reacted with uridine 5'-monophospho morpholidate 4-morpholine-N,N'-dicyclohexylcarboxamidine salt (296 mg, 404 μmol) and 1H-tetrazole (57 mg, 808 μmol) in dry pyridine (1.25 mL) as described for 32. Purification on a Bio-Gel P-2 column (2.5×95 cm), eluated with 250 mM $NH_4HCO_3$, and precipitation from $H_2O$/MeOH/acetone gave 34 (134 mg, 91%) as a white solid after lyophilization ($R_f$ 0.40, 2:1 i-PrOH/1M $NH_4OAc$). The $^1H$ NMR spectral data were in agreement with the published ones (Heidlas et al. *J. Org. Chem.* 1992, 57, 152–157).

Synthesis of Compound 36 as illustrated in FIG. 13.

Step 1) A mixture of L-fucose (1.0 g, 6.0 mmol) and benzyl chloride (3.4 mL, 36 mmol) in pyridine (5 mL) was stirred overnight at rt. The mixture was concentrated to an oil, which was coevaporated three times with toluene. The residue was purified by silica gel chromatography (2:1 hexane-EtOAc) to give product carried onto the next step (1.26 g, 72%).

Step 2) A solution of HBr in HOAc (10 mL) was added dropwise into a solution of the above product (1.22 g, 4.17 mmol) in $CH_2Cl_2$ (25 mL) and $Ac_2O$ (2.5 mL) at 0° C. The solution was stirred for 2 h at 0° C., warmed to rt, and stirred an additional 1 h. The reaction mixture was poured on ice-cold water and extracted with $CH_2Cl_2$ (2×50 mL). The combined extracts were washed with sat. $Na_2CO_3$ (2×100 mL) and brine. The organic layer was dried ($MgSO_4$) and evaporated to yield the title compound (1.29 g, 99%) as a light yellow syrup used in the subsequent step without purification ($R_f$ 0.47, 2:1 hexane-EtOAc).

Step 3) 2,3,4-tri-O-benzyl-α-L-fucopyranosyl bromide (500 mg, 1.60 mmol; vida supra), having been coevaporated twice with benzene, was dissolved in dry benzene (28 mL) and stirred with 4Å molecular sieves for 30 min at rt. Dibenzyl phosphate (1.33 g, 4.79 mmol) and $Ag_2CO_3$ (0.88 g, 3.19 mmol) were added and the solution was stirred for 30 h in the dark. The mixture was filtered and concentrated. Silica gel chromatography (1:1 hexane-EtOAc) yielded 36 (724 mg, 89%) as a light yellow syrup ($R_f$ 0.37, 1:1 hexane-EtOAc).

Synthesis of Compound 37 as illustrated in FIG. 13.

Step 1) The fully protected sugar phosphate 36 (692 mg, 1.36 mmol) was dissolved in a mixture of toluene (8 mL), pyridine (1.5 mL), and $Et_3N$ (1.2 mL). 10% palladium on carbon (60 mg) was added and the solution stirred under an hydrogen atmosphere for 14 h. The mixture was filtered, evaporated, and coevaporated with toluene to yield the intermediate product;

Step 2) Crude product (577 mg; vida supra) was dissolved in MeOH (5 mL), and cyclohexylamine (5 mL) was added, forming a precipitate. The mixture was heated to reflux for 1.5 h, during which the solution clarified, and the product finally precipitated. After 4.5 h, the mixture was cooled to rt, filtered, and the precipitate (a white solid) was washed three times with chloroform and dried (465 mg). The filtrate was evaporated to dryness, dissolved in water, washed three times with chloroform, and evaporated to yield a white solid. Recrystalization of filtrate residue from hot ethanol yielded an additional 87 mg, to give a total 552 mg (95% overall yield) of product 37.

$^{31}P$ NMR spectroscopical monitoring of morpholidate couplings (chart shown in FIG. 15).

Guanosine 5'-monophospho morpholidate 4-morpholine-N,N'-dicyclohexylcarboxamidine salt (1.01 g, 1.28 mmol) and internal standard triphenylphosphine oxide (44.5 mg, 160 μmol) were coevaporated with dry pyridine (4×5 mL), dried under vacuum for 2 d, and dissolved in pyridine/DMSO-$d_6$ (7:3, 3.9 mL). This stock solution was the same for all following reactions. Triethylammonium β-L-fucopyranosyl phosphate 29 (36.2 mg, 100 μmol) was coevaporated with dry pyridine (3×1.5 mL) and dried under vacuum for 2 d. GMP-morpholidate stock solution (500 μL) and 3.2 equiv. (320 μmol) of the additive, i. e. 1H-tetrazole (22 mg), 1,2,4-triazole (22 mg), acetic acid (18 μL), NHS (37 mg), DMAP.HCl (51 mg), or $HClO_4$ (19 μL), respectively, were added. The resulting solution was transferred into a 5-mm NMR tube via syringe and the reaction was followed by proton coupled $^{31}P$ NMR spectroscopy using a pulse angle of 60° and a relaxation delay of 5 sec. Collection of 64 transients gave adequate spectra. Signals at δ 4.95 (GMP-morpholidate), 0.29 (GMP), −0.73 (29), and −13.38 ppm (30) were integrated and referenced to the integral of internal standard triphenylphosphine oxide whose concentration was assumed to stay constant.

What is claimed:

1. A process for preparing a 2-deoxy-2-fluoro-glycosyl-pyranosyl phosphate comprising the following steps:

Step A: fluorohydrinating a glycal with a fluoridating agent and a hydroxylating agent for producing a 2-deoxy-2-fluoro-glycoside; and then Step B: phosphorylating the 2-deoxy-2-fluoro-glycoside with a phosphorylating agent for producing a 2-deoxy-2-fluoro-glycosyl-pyranosyl phosphate.

2. A process for preparing a nucleotide-linked-2-deoxy-2-fluoroglycoside comprising the following steps:

Step A: phosphorylating a 2-deoxy-2-fluoro-glycoside with a phosphorylating agent for producing a 2-deoxy-2-fluoro-glycosyl-pyranosyl phosphate; and then Step B: coupling the 2-deoxy-2-fluoro-glycosyl-pyranosyl phosphate to a nucleotide with a coupling agent for producing the nucleotide-linked-2-deoxy-2-fluoroglycoside.

3. A process for preparing a nucleotide-linked-2-deoxy-2-fluoroglycoside comprising the following steps:

Step A: fluorohydrinating a glycal with a fluoridating agent and a hydroxylating agent for producing a 2-deoxy-2-fluoro-glycoside; then Step B: phosphorylating the 2-deoxy-2-fluoro-glycoside with a phosphorylating agent for producing a 2-deoxy-2-fluoro-glycosyl-pyranosyl phosphate; and then Step C: coupling the 2-deoxy-2-fluoro-glycosyl-pyranosyl phosphate to a nucleotide with a coupling agent for producing the nucleotide-linked-2-deoxy-2-fluoroglycoside.

4. A process as described in claim 3 wherein the nucleotide-linked-2-deoxy-2-fluoroglycoside is selected from the group consisting of uridine 5'-diphospho-2-deoxy-2-fluoro-D-galactose, guanosine-5'-diphospho-2-deoxy-2-fluoro-L-fucose, uridine-5'-diphospho-2-deoxy-2-fluoro-D-glucose, guanosine-5'-diphospho-2-deoxy-2-fluoro-D-mannose, cytosine-5'-monophospho-2-deoxy-2-fluoro-sialic acid and cytosine-5'-monophospho-2-deoxy-2-2-keto-3-deoxyoctonate (KDO).

5. A process as described in claim 4 wherein the glycal is selected from the group consisting of D-galactal, L-fucal, tri-O-acetyl-D-glucal, sialic acid glycal, KDO glycal.

6. A process as described in claim 5 wherein the fluoridating agent is $XeF_2$.

7. A process as described in claim 6 wherein the hydroxylating agent is water.

8. A process as described in claim 7 wherein the 2-deoxy-2-fluoro-glycoside is selected from the group consisting of 2-deoxy-2-fluoro-D-galactose, 2-deoxy-2-fluoro-L-fucose, 2-deoxy-2-fluoro-D-glucose, 2-deoxy-2-fluoro-D-mannose, 2-deoxy-2-fluorosialic acid, 2-deoxy-2-fluoro-KDO.

9. A process as described in claim 8 wherein the phosphorylating agent is selected from the group consisting of ATP with glycosylkinase and dibenzyl phosphate.

10. A process as described in claim 9 wherein the 2-deoxy-2-fluoro-glycosyl-pyranosyl phosphate is selected from the group consisting of 2-deoxy-2-fluoro-α-D-galactopyranosyl phosphate, 2-deoxy-2-fluoro-α-L-fucosylpyranosyl phosphate, 2-deoxy-2-fluoro-D-glucosylpyranosyl phosphate, 2-deoxy-2-fluoro-D-mannosylpyranosyl phosphate, 2-deoxy-2-fluoro-sialic acid-pyranosyl phosphate, 2-deoxy-2-fluoro-KDO-pyranosyl phosphate.

11. A process as described in claim 10 wherein the nucleotide is selected from the group consisting of uridine 5'-diphosphate, guanosine 5'-diphosphate, adenosine 5'-diphosphate and cytidine 5'-diphosphate.

12. A process as described in claim 11 wherein the coupling agent is selected from the group consisting of galactose-1-phosphate uridyl transferase, guanosyl-monophosphate (GMP)-morpholidate, cytidyl-mono-phosphate (CMP)-morpholidate and uridyl-mono-phosphate (UMP)-morpholidate.

13. A process for preparing a 2-deoxy-2-fluoro-glycoside as described in claim 4 wherein the glycal is admixed with $XeF_2$ followed by hydrolysis with hydrochloric acid for producing the 2-deoxy-2-fluoro-glycoside.

14. A process for preparing the 2-deoxy-2-fluoro-glycosyl-pyranosyl phosphate as described in claim 13 wherein the 2-deoxy2-fluoro-glycoside is activated with acetic anhydride and then hydrobromic acid followed by phosphorylation with dibenzyl phosphate and reduction using hydrogen with Pd/C for producing the 2-deoxy-2-fluoro-glycosyl-pyranosyl phosphate.

15. A process for preparing the nucleo de-linked-2-deoxy-2-fluoroglycoside as described in claim 14 wherein the 2-deoxy-2-fluoro-glycosyl-pyranosyl phosphate is converted into a phosphate ion followed by coupling a nucleotide linked morpholidate to the phosphate ion in the presence of 1H-tetrazole wherein the nucleotide linked morpholidate is selected from the group consisting of guanosyl-mono-phosphate (GMP)-morpholidate, cytidyl-mono-phosphate (CMP)-morpholidate and uridyl-mono-phosphate (UMP)-morpholidate for producing the nucleotide-linked-2-deoxy-2-fluoroglycoside.

16. A process for preparing uridine 5'-diphospho-2-deoxy-2-fluoro galactose comprising the steps of:

Step A: fluorohydrinating D-galactal with $XeF_2$ and water for producing 2-deoxy-2-fluoro-galactose; then Step B: phosphorylating 2-deoxy-2-fluoro-galactose with ATP and galactokinase for producing 2-deoxy-2-fluoro-α-D-galactopyranosyl phosphate; and then Step c: coupling 2-deoxy-2-fluoro-α-D-galactopyranosyl phosphate with uridine 5'-diphosphate using galactose-1-phosphate uridyl transferase for producing uridine 5'-diphospho-2-deoxy-2-fluoro galactose.

17. A process as described in claims 16 wherein D-galactal is admixed with $XeF_2$ and water at room temperature followed by neutralization with potassium carbonate for producing 2-deoxy-2-fluoro-D-galactose.

18. A process as described in claim 17 wherein 2-deoxy-2-fluoro-D-galactose (2FGal) is admixed with ATP, phospho(enol)pyruvate, galactokinase and pyruvate kinase in a pH 7.4 buffer solution at room temperature for producing 2-deoxy-2-fluoro-α-D-galactopyranosyl phosphate (2FGal-1P).

19. A process as described in claim 18 wherein 2-deoxy-2-fluoroα-D-galactopyranosyl phosphate (2FGal-1P) is admixed with UTP, UDP glucose, galactose-1-phosphate uridyl transferase, uridine 5'-diphosphoglucose pyrophosphorylase and inorganic pyrophosphatase in a pH 8.4 buffer solution at room temperature for 3 days for producing uridine 5'-diphospho-(2-deoxy-2-fluoro)galactose (UDP-2F-Gal).

20. A process for preparing a nucleotide-linked-2-deoxy-2-fluoroglycoside comprising the following steps:

Step A: fluorohydrinating a glycal with a fluoridating agent and a hydroxylating agent for producing a 2-deoxy-2-fluoro-glycoside; and then Step B: coupling the 2-deoxy-2-fluoro-glycosyl-pyranosyl phosphate to a nucleotide with a coupling agent for producing the nucleotide-linked-2-deoxy-2-fluoroglycoside.

21. A process as described in claim 20 wherein the nucleotide-linked-2-deoxy-2-fluoroglycoside is selected from the group consisting of cytosine-5'-monophospho-2-deoxy-2-fluoro-D-sialic acid and cytosine-5'-monophospho-2-deoxy-2-KDO.

22. A process as described in claims wherein the glycal is selected from the group consisting of sialic acid glycal and KDO glycal.

23. A process as described in claim 22 wherein the fluoridating agent is $XeF_2$.

24. A process as described in claim 23 wherein the hydroxylating agent is water.

25. A process as described in claim 24 wherein the 2-deoxy-2-fluoro-glycoside is selected from the group consisting of 2-deoxy-2-fluorosialic acid and 2-deoxy-2-fluoro-KDO.

26. A process as described in claim 25 wherein the coupling agent is selected from the group consisting of cytidyl-mono-phosphate (CMP)-sialate synthetase, cytidyl-mono-phosphate (CMP)-KDO-synthetase.

27. A process as described in claim 26 wherein the nucleotide is cytidine 5'-phosphate.

* * * * *